United States Patent
Quatrano et al.

(10) Patent No.: US 9,243,261 B2
(45) Date of Patent: Jan. 26, 2016

(54) PLANTS HAVING INCREASED DESICCATION TOLERANCE, INCREASED DROUGHT TOLERANCE OR INCREASED WATER USE EFFICIENCY

(71) Applicants: Ralph S. Quatrano, St. Louis, MO (US); Yoichi Sakata, Tokyo (JP); Izumi Yotsui, Tokyo (JP)

(72) Inventors: Ralph S. Quatrano, St. Louis, MO (US); Yoichi Sakata, Tokyo (JP); Izumi Yotsui, Tokyo (JP)

(73) Assignee: Washington University, St Louis, MI (US)

( * ) Notice: Subject to any disclaimer, the term of this patent is extended or adjusted under 35 U.S.C. 154(b) by 276 days.

(21) Appl. No.: 13/919,300

(22) Filed: Jun. 17, 2013

(65) Prior Publication Data

US 2014/0020132 A1  Jan. 16, 2014

Related U.S. Application Data

(60) Provisional application No. 61/660,277, filed on Jun. 15, 2012.

(51) Int. Cl.
*C12N 15/82* (2006.01)
*C07K 14/415* (2006.01)

(52) U.S. Cl.
CPC .......... *C12N 15/8273* (2013.01); *C07K 14/415* (2013.01); *C12N 15/8293* (2013.01)

(58) Field of Classification Search
None
See application file for complete search history.

(56) References Cited

U.S. PATENT DOCUMENTS

| | | | |
|---|---|---|---|
| 5,378,619 | A | 1/1995 | Rogers |
| 6,054,635 | A | 4/2000 | Bestwick et al. |
| 6,664,387 | B2 | 12/2003 | Chung et al. |
| 2008/0282431 | A1 | 11/2008 | Dasgupta et al. |
| 2008/0313776 | A1 | 12/2008 | Li |

FOREIGN PATENT DOCUMENTS

| | | |
|---|---|---|
| JP | 2002/238564 | 8/2002 |
| WO | WO 00/37662 | 6/2000 |

OTHER PUBLICATIONS

Guo et al (2004, Proc. Natl. Acad. Sci. USA 101: 9205-9210).*
Andrews (Biochimica et Biophysica Acta 1800 (2010) 691-705).*
Bartels et al., Desiccation Tolerance: Gene Expression, Pathways, and Regulation of Gene Expression, Plant Desiccation Tolerance, 2007, pp. 115-137, vol. 5.
Benfey et al., The Cauliflower Mosaic Virus 35S Promoter: Combinatorial Regulation of Transcription in Plants, Science, 1990, pp. 959-966, vol. 250 No. 4983.
Charron et al., Between a rock and a dry place: the water-stressed moss, Mol Plant, 2009, pp. 478-486, vol. 2.
Cushman et al., Understanding Vegetative Desiccation Tolerance Using Integrated Functional Genomic Approaches Within a Comparative Evolutionary Framework, Plant Desiccation Tolerance, Ecological Studies, 2011, pp. 207-338, vol. 215.
Dillon et al., RNAi as an Experimental and Therapeutic Tool to Study and Regulate Physiological and Disease Processes, Annu. Rev. Physiol., 2005, pp. 147-173, vol. 67.
Dykxhoorn et al., The Silent Revolution: RNA Interference as Basic Biology, Research Tool, and Therapeutic, Annu., Rev. Med., 2005, pp. 401-423, vol. 56.
Elhai et al., Conjugal Transfer of DNA to Cyanobacteria, Methods in Enzymology,1988, pp. 747-754, vol. 167.
Eriksson et al., Dehydrins: Molecular Biology, Structure and Function, Plant Desiccation and Tolerance, Ecological Studies, 2011, pp. 289-305, vol. 215.
Ghadessy et al., Directed evolution of polymerase function by compartmentalized self-replication, PNAS, 2001, pp. 4552-4557, vol. 98, No. 8.
Grene et al., Molecular Biology and Physiological Genomics of Dehydration Stress, Plant Desiccation Tolerance, Ecological Studies, 2011, pp. 255-287, vol. 215.
Helene et al., Control of Gene Expression by Triple Helix-Forming Oligonucleotides, The antigene Strategy. Ann. NY Acad. Sci., 1992, pp. 27-36, vol. 660.
Holtorf et al., Promoter subfragments of the sugar beet V-type $H^+$-ATPase subunit c isoform drive the expression of transgenes in the moss *Physcomitrella patens*, Plant Cell Rep., 2002, pp. 341-346, vol. 21.
Horstmann et al., Quantitative promoter analysis in *Physcomitrella patens*: a set of plant vectors activating gene expression within three orders of magnitude, BMC Biotechnology, 2004, pp. 1-13, vol. 4.
Jost et al., Isolation and characterization of three moss-derived beta-tubulin promoters suitable for recombinant expression, Curr Genet, 2005, pp. 111-120, vol. 47.
Khandelwal et al., Role of ABA and ABI3 in Desiccation Tolerance, Science, 2010, pp. 546, vol. 327.
Lee et al., Aptamer therapeutics advance, Current Opinion in Chemical Biology, 2006, pp. 282-289, vol. 10.
Link et al., Beyond toothpicks: new methods for isolating mutant bacteria, Nature Reviews, 2007, pp. 680-688, vol. 5.
Malik et al., A constitutive gene expression system derived from the *tCUP* cryptic promoter elements, Theor Appl Genet, 2002, pp. 505-514, vol. 105.
Marella et al., Characterization and functional analysis of *Abscisic Acid Insensitive*3-like genes from *Physcomitrella patens*, The Plant Journal, 2006, pp. 1032-1044, vol. 46.
Perroud et al., BRICK1 Is Required for Apical Cell Growth in Filaments of the Moss *Physcomitrella patens* but Not for Gametophore Morphology, The Plant Cell, 2008, pp. 411-422, vol. 20.
Pushparaj et al., Short Interfering RNA (siRNA) as a Novel Therapeutic, Clin. Exp. Pharm. and Phys., 2006, pp. 504-510, vol. 33.
Reynolds et al., Rational siRNA design for RNA interference, Nature Biotechnology, 2004, pp. 326-330, vol. 22, No. 3.

(Continued)

*Primary Examiner* — Anne Kubelik
*Assistant Examiner* — Charles Logsdon
(74) *Attorney, Agent, or Firm* — Dentons US LLP

(57) ABSTRACT

A transgenic plant engineered to have increased desiccation tolerance, increased drought tolerance or increased water use efficiency, the plant transformed with an artificial DNA construct comprising a transcribable nucleic acid molecule encoding a polypeptide requiring both ABA and ABI3 to influence desiccation tolerance. Also provided are DNA constructs and methods of producing a transgenic plant engineered to have increased desiccation tolerance, increased drought tolerance or increased water use efficiency.

14 Claims, 5 Drawing Sheets

(56) References Cited

OTHER PUBLICATIONS

Sagner et al., Rapid filter assay for the detection of DNA polymerase activity: direct identification of the gene for the DNA polymerase from *Thermus aquaticus*, Gene, 1991, pp. 119-123, vol. 97.

Saidi et al., Controlled expression of recombinant proteins in *Physcomitrella patens* by a conditional heat-shock promoter: a tool for plant research, Plant Molecular Biology, 2005, pp. 697-711, vol. 59.

Stavolone et al., Cestrum yellow leaf curling virus (CmYLCV) promoter: a new strong constitutive promoter for heterologous gene expression in a wide variety of crops, Plant Molecular Biology, 2003, pp. 703-713, vol. 53.

Studier, Protein production by auto-induction in high-density shaking cultures, Protein Expression & Purification, 2005, pp. 207-234, vol. 41.

Weise et al., Use of *Physcomitrella patens* actin 5' regions for high transgene expression: importance of 5' introns, Appl Microbiol Biotechnol, 2006, pp. 337-345, vol. 70.

Werner et al., Abscisic-acid-induced drought tolerance in Funaria hygrometrica Hedw., Planta, 1991, pp. 99-103, vol. 186.

Wood et al., Plant Desiccation Tolerance: Diversity, Distribution, and Real-World Applications, Plant Desiccation Tolerance, 2007, pp. 3-8, vol. 1.

Yotsui et al., Abscisic Acid Insensitive3 regulates abscisic acid-responsive gene expression with the nuclear factor Y complex through the ACTT-core element in *Physcomitrella patens*, New Phytologist, 2013, pp. 101-109, vol. 199.

You et al., Use of Bacterial Quorum-Sensing Components to Regulate Gene Expression in Plants, Plant Physiology, 2006, pp. 1205-1212, vol. 140.

Zeidler et al., Tetracycline-regulated reporter gene expression in the moss *Physcomitrella patens*, Plant Molecular Biology, 1996, pp. 199-205, vol. 30.

\* cited by examiner

SEQUENCE LISTING

<160> NUMBER OF SEQ ID NOS: 8

<210> SEQ ID NO 1
<211> LENGTH: 588
<212> TYPE: DNA
<213> ORGANISM: Physcomitrella patens

<400> SEQUENCE: 1

| | | | | | |
|---|---|---|---|---|---|
| atggcaacag | tgaacggtac | atcaataatg | cagactacca | acttagcaat | cacacccgtg | 60 |
| gctgcaagcc | atttgggctc | gcgcaccgtc | cagctcggag | tcacgcgcgt | actctacaac | 120 |
| gccaccctta | ccaccaggtc | tgcaaggagg | ctcgtcgtgg | tcgccgccgg | aaacccggaa | 180 |
| cgaattgaca | acttcgtcga | cggagccagg | aaagacgcca | gccaaaacgc | gaagaacttc | 240 |
| ggcaaccagg | tggcggacgc | cttcggcaac | gcccaggaga | ccgcgaagga | cgtgggtcgg | 300 |
| gacatgggcg | ccaaggcaca | ggaagccgtc | gaccaaggca | gtaagaaggt | cgacgaggca | 360 |
| ggagacaagg | ccagggatgt | agccaaggaa | gtgagggct | ccaccgagga | taccttgaat | 420 |
| gctgccaaag | caaacaacgg | ccaatctgtt | gcggacaagg | cgcaaaatgc | tgcatccaac | 480 |
| gtgggtgaca | atttgaagca | gaacttcgat | tacggaactg | gggccgtgca | gaacgccgcc | 540 |
| gatgacgcga | gcaaaaacgt | gaaagacgcc | actaaccgca | acctctag | | 588 |

<210> SEQ ID NO 2
<211> LENGTH: 264
<212> TYPE: DNA
<213> ORGANISM: Physcomitrella patens

<400> SEQUENCE: 2

```
atgtcgagcc aggaagatct tgacgccaag gccgccgctg agagacggt ggtgcccgga      60
ggcactggcg gaaggtcctt tcaagctcag aagaaccttg cagaaggccg cagcaaagga     120
gggcaagctc gtgcggagca gctgggtcat gaaggatacg tagagatggg caagaaggga     180
ggctctgcta caactgacat gtccagtgga ggcgctgccg aggctgccgg tcgcggcatc     240
gacgagacca agttcaccac ctag                                            264
```

<210> SEQ ID NO 3
<211> LENGTH: 708
<212> TYPE: DNA
<213> ORGANISM: Physcomitrella patens

<400> SEQUENCE: 3

```
atgaagatga cggtggttgc ggtgatggcc gtggttctga tcctcggtag cgagctgcct      60
cgctactcga gcgcagtttc gagcgaggct gaggagtttg tgtcagcgca caacgcagcg     120
agggctgatg tggacgtagg gcctttggtt tggagccaca agctggagga ttacgcgcgc     180
aagtacgggg aggagcagcg cgatcatcac aattgcgcca tggtgcactc gcggggtccg     240
tatggggaga ccttttctg gggctacggg aagtcgtttg cgcccgcgga tgccgtgcgc     300
tcgtgggtgg atgagaaaca gcactacgac tacgactcga attcctgcgc gtcggggaag     360
gtgtgcgggc actatacgca ggtggtgtgg gcggacacaa aggaggtcgg gtgcgcttca     420
atcacctgcc atgacaaggc cacgttcatc atctgcagct ataatccgcc tggcaacttc     480
gtgggcgaat ggccatacaa gcgtgccgga accaagcatt cacataggcg atctcatgaa     540
aacgacgact ctcgcacaag ctcccataaa accacagccc agaccacaga cgatgccaac     600
tccgacctca agctccgctc agtacatgag tgtatgagcc agtgtatgaa tgattgcttc     660
tcgatgtctg gtccagcca tcaccatcgc tcgaactact atcagtag                    708
```

<210> SEQ ID NO 4
<211> LENGTH: 1227
<212> TYPE: DNA
<213> ORGANISM: Physcomitrella patens

<400> SEQUENCE: 4

```
atggctaatc ggtacttccc caacactatg ccagattatt cattgagttt ggaaggctca      60
gaagcggatt attcagtgat ggatcctgac acgctgctgg aggtcgccat gtccatcaaa     120
gatgaggtga tacaagcaac atggatacga aaaggccgaa gggtttctga ccccattctc     180
tacacagggg tgttgggaac agcttttctg tgctttaagg catatcaaat acaggaagc     240
aaagaggatc tcacactctg cagcgagatc gttgatagtt gtaccgttgc cgctaaatct     300
ttgcacaaat acgtcacttt tttatgtggg cagccaggca tatatgcctt aggagcagca     360
gcggcaaaaa gcagcgggga tgagcaaagt cttcatcgat atcttcagct tttccataag     420
gtttccaaaa accaaactct tgctgtggga gcggaagagg tggtatggg aatgccttac     480
gaacttttat atggacgtgc ggggttctta tgggctgctc tctttgtcaa caagcatgtc     540
ggcgagggga ccattccttc gagcactacg gtcccatag ttgatgcgat tttagctggc     600
ggacgagctg gagcttcaca aacacagtct ccattgatgt atcagtggca cggatcaaga     660
```

| | |
|---|---:|
| tattggggag gagcacatgg tctggctggt atcatgcaca ctctcatgca ctttcccttg | 720 |
| aacaaaaaag atgaagagga tgtcaaggga cactacgat acatgatcgc gcgccgcttt | 780 |
| cctagtggca actacccatc cagcgagggc aatgcaacag accggttggt gcattggtgc | 840 |
| cacggagcac ctggtattgc catgactttg tgcaaggcgt ctaaggtatt tcctgatgaa | 900 |
| atggagttcc aacatgcagc agttgaagca ggagatgtcg tatggagtcg aggtctactt | 960 |
| cggaagttgg gcctctgtca tgggatcagt ggaaatacct acgtctttct gtctttgtac | 1020 |
| caatcaacag gagggaaaca gcacctcttc agagctcaac aattcgccac tttccttcac | 1080 |
| aaaaacgcca gaacgttgat cgagtcagga gagatgcacg gcggtgacca tccctactct | 1140 |
| ctgtttgaag gcttggcagg aactgcatgc ctctttttg acttgacaaa accagagatg | 1200 |
| gcaagattcc ctgcttatga gctttag | 1227 |

<210> SEQ ID NO 5
<211> LENGTH: 1200
<212> TYPE: DNA
<213> ORGANISM: Physcomitrella patens

<400> SEQUENCE: 5

| | |
|---|---:|
| atggcatcgt acaagaggac ctgtacaagt ggcaacacgg cttgctgggc actggacaca | 60 |
| tcaaatggat tgcatgacgc tctctggggc cttgtcgtca tgcaccaccg caatggccat | 120 |
| tacccgagtc tggaagcatc gctagcattt cgatcctctc cctcgccttc aaaacctccg | 180 |
| gggaacactc caaccatcgc agtcgtcatt caagtgaatt ccattctcgt attgcaccga | 240 |
| acaagaactt ttctgttgac cagtgatctt gaatctttcg taaattttag ctgtagtcgg | 300 |
| atttacgttt tcgcaatggc ggaattccga cccgcacaag agcagtcgca gcaccctgga | 360 |
| gaggagcatt tgatggatcc tgtgcctcgt caccacggaa ccaactacaa ggctgctggc | 420 |
| aagttgaagg gaaagatagc tctagtgaca ggcggtgact ccggcatagg tcgtgccgtg | 480 |
| ggcgtgctct tcacacgaga aggtgccaca gtggccttca catatgtgaa aggagcggaa | 540 |
| gaaaagatg cggtagacac gattaatttg ctgaagcagt acaaggcaga aggtggtggc | 600 |
| gaaggagaac ctcttgcaat tccctgcgat ctaggattcg acgagcagtg caagaaggtt | 660 |
| gtagacaaag tcgttgagaa gtatggccga atcgacatcc tggtcaacaa tgcggcagag | 720 |
| cagcacgtcg tggagaacat tgaggatctc cagcctgagc agctggagcg acgttccgc | 780 |
| accaacatct tctcccagtt ttacctcgta agacatgcct tgaagcatat gaaagagggt | 840 |
| agctgtatta ttaatacgac ttccgttaat gcattcaagg gcaacaccac acttctagac | 900 |
| tacacttcca caaagggcgc cattcttgcc ttcactcggg gactggctct tcagcttgtc | 960 |
| aagcgcggaa ttgagtaaa tgcggtagcg ccaggcccaa tttggacgcc gctcattcca | 1020 |
| gcatcaatgg gtcaaggatc gcctgagaag atgaaatcct tcggttcgca atgcccaatg | 1080 |
| ggccgtgctg gtgagccaga ggaaatcgca acggcgtatg ttttccttgc ttcagaggat | 1140 |
| tcctcttact tcactggcca aaccctgcac ccgaacggtg aatagttgt gaacgcataa | 1200 |

<210> SEQ ID NO 6
<211> LENGTH: 963
<212> TYPE: DNA
<213> ORGANISM: Physcomitrella patens

<400> SEQUENCE: 6

| | |
|---|---:|
| atggtgaatc aagcattgga ggctatgccg aagcttaagt tgaacactgg cacatgtatt | 60 |
| tccgccgttg ggctaggaac ctggcaggcg gatccaggct tggttaaaca agctgtcaag | 120 |

```
gaagctgtaa aagttgggta ccgccacatc gactgcgcca aggcttacaa aaacgaggac    180
gaggtgggag aagctttgca ggagcttttc aaggaaggcg ttgttaagcg tgaagacttg    240
tggatcacgt cgaaactttg gtgcactgac cacaaccctg cggatgtgga gccggcattg    300
gacgggtcga ttgagcgttt gcaatgtggc taccttgatc tgtacctgat gcattggccg    360
gtcgccttga agaaggatgc tcaaggcaca ggtccagatg actttgctcc tctcaatgtc    420
gcggcgacat gggcagctat ggaaaagtgc tacgagaagg ggaaagcgaa ggctatcgga    480
atcagtaact tctctgtaga gaaaacgaag gacttgttgt ctaaatgcaa agtacgacct    540
gctgtgaacc aggtggaatg ccaccctctt tggcagcaga agaagttgtg gccatactta    600
aagtccgagg gcattcactt gacagcttac tctccaatcg gatcctcaaa cagtcccttc    660
gcaacaatta acgtcttaga gcttccacca gtcacgaaat ggctgagaa atacaaaagg    720 tctccatcac agatagttct ccgatggaac atccaacaag gtcatagcgt gctgccaaag    780
agcactcacg ctgatcggct tgcgtccaac attgagatct tcgacttcga actcaatgaa    840
gaagatctca aggaattcga caaaattgag cagcaccgcc ttctccttgg agacgacatg    900
tggataaatg acaaaaccag tccatacaag acggtggagg agctctggga cggagacatc    960
taa                                                                    963

<210> SEQ ID NO 7
<211> LENGTH: 663
<212> TYPE: DNA
<213> ORGANISM: Physcomitrella patens

<400> SEQUENCE: 7
atggcgaagt ccgccgccgc cgtggtgata tgtgtgcttt tcttgggggt gttcatgggg     60
actcctgctg tggcgagcag gaagatgtgc aaaggagcgg tttccctcgc cattcgtgcg    120
ctttgcattc ctacgacaga gtcgttgttc atgaagcacg atgggaagca ctcgtgcgcg    180
tataatttga ctaacggtga cagagctgtt ggtgtggcgt ataacttgga tgatgacgta    240
gagtctcgcc ggtctgagct tactgctgtt tttgctgact acgacaaggt ttacgaaggg    300
aaagactgcc tgaacacaat ccagattagt gccctgctca ctttagatgc taaacgtgcc    360
cttgatagag ctgccaaaag cgttaagtcc ttagacgacc agtgctgcga cgtcatggcc    420
gtttttggcg acatccaaca ctctggaggc aaggacgtgt accaggaaaa tgcgtttgat    480
gacttcattg aagctgtgag tgccaagaaa tgggagaagg gagtcgagtt gctggataga    540
accaggtggt gcaatgacaa caagatagat gtgatgacg ataaaaagat catctctgaa    600
ggttgcaagg gtacattcgc cactggagtc attgctcagg tcaccgacgc tctgaaagct    660
tag                                                                    663

<210> SEQ ID NO 8
<211> LENGTH: 993
<212> TYPE: DNA
<213> ORGANISM: Physcomitrella patens

<400> SEQUENCE: 8
atgatgggta ctcggaacgt gttggttttt gctgttgggt tgtttcttgt gctgagcttt     60
gctgcagcta gcggcagtaa acatgacgac aaccatgagc tgatgatcgg ggggctggac    120
atcgactaca gtgccggcc cgggaactat accaccacca aggacaagga gctcacgcag    180
gttgctctga acttggagta tttcgaagcg gagtattttct tgtggggagc ttacggctat    240
```

```
ggtttggaca agattgctcc ctacttggtc gatggcggtc ccccccccat tggtgctcag    300
aaggccaatt tggacgctta ctataccgat atctacattc agatggggct tcaggaagtt    360
ggacatctca gggcgatcaa gagagctttg ggtgatcctc ccaggtgtgc attccctcgc    420
actcagctgg acattagcaa aaagacctgg gccgatacga tggacaaggc gttcctgcag    480
actttcggcg agaagctgaa ccctccctat gatccttatg aagacagctt gaagtacctc    540
atctccacgt acaccattcc ctacgttggg ttgacgggat acgtcggcgc taaccccgag    600
ttgaagggat acaatgccaa gaagcttgtg gctggtttgc tgggtgtgga gtcgggtcaa    660
gacgctatca ttcgcaccga aatgtaccgc cagaagaaca agaaggtcag cccgtacaag    720
tacaccgtgg cggatttcag caacgccatt tccaacttga ggaacaactt gtcccacgct    780
ttcgttgacg aaggattggt ggtgccaaat gagctgggtg ctgaaatgat ggtgactggt    840
aacatattgt ctgctgacaa cgactctctc tcctaccctc gtactgccga gcaggtgttc    900
gaaactgttt acgggaccgg agatgcttcc aagcccggag gcttctatcc caagggctgt    960
cagggtgtca tcgccgcgag ttaccttgat tag                                 993
```

US 9,243,261 B2

PLANTS HAVING INCREASED DESICCATION TOLERANCE, INCREASED DROUGHT TOLERANCE OR INCREASED WATER USE EFFICIENCY

CROSS-REFERENCE TO RELATED APPLICATIONS

This application claims priority from U.S. Provisional Application Ser. No. 61/660,277 filed on 15 Jun. 2013, which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

To survive on land, the earliest land plants had to develop mechanisms to tolerate desiccation. Modern seed plants possess an array of morphological features to retain water (such as conductive tissues, waxy layers on leaves, and openings in leaves that can be control to prevent water loss) and have retained desiccation tolerance in only a few specialized structures (e.g., seeds). Present-day bryophytes (mosses), in contrast, lack water transport and retention tissues, presumably like early land plants. As a result, their normal state is at equilibrium with the surrounding air, creating a water-deficit condition that most seed plants could not tolerate.

The plant specific transcription factor ABSCISIC ACID INSENSITIVE3 (ABI3) functions in ABA signaling during seed maturation and germination. It has been reported that ABI3 is evolutionarily conserved in the non-seed plant *Physcomitrella patens*. Furthermore, both ABA and ABI3 are required for *P. patens* vegetative tissue to survive desiccation.

SUMMARY OF THE INVENTION

Among the various aspects of the present disclosure is the provision of a transgenic plant engineered to have increased desiccation tolerance, increased drought tolerance or increased water use efficiency. In some embodiments, the plant transformed with an artificial DNA construct comprising, as operably associated components in the 5' to 3' direction of transcription: a promoter that functions in a plant; a polynucleotide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a sequence at least 95% identical thereto; and a transcriptional termination sequence; wherein the transgenic plant has an increased desiccation tolerance compared to a plant without the DNA construct. In some embodiments, the transgenic plant has increased desiccation tolerance. In some embodiments, the transgenic plant has increased drought tolerance. In some embodiments, the transgenic plant has increased water use efficiency. In some embodiments, the transgenic plant has two or more of increased desiccation tolerance, increased drought tolerance or increased water use efficiency.

In some embodiments, the transgenic plant has all of increased desiccation tolerance, increased drought tolerance and increased water use efficiency.

In some embodiments, the DNA construct comprises a polynucleotide of SEQ ID NO: 8, or a sequence at least 95% identical thereto.

In some embodiments, the DNA construct comprises at least two polynucleotides independently selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a sequence at least 95% identical thereto. In some embodiments, the plant comprises at least two DNA constructs, each DNA construct comprising a polynucleotide independently selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a sequence at least 95% identical thereto.

In some embodiments, the plant comprises SEQ ID NO: 8 and one or more of SEQ ID NO: 1, SEQ ID NO: 2, SEQ ID NO: 3, SEQ ID NO: 4, SEQ ID NO: 5, SEQ ID NO: 6, or SEQ ID NO: 7. In some embodiments, the plant comprises SEQ ID NO: 8 and one or more of SEQ ID NO: 1, SEQ ID NO: 2, or SEQ ID NO: 5. In some embodiments, the plant comprises: SEQ ID NO: 8 and SEQ ID NO: 1; SEQ ID NO: 8 and SEQ ID NO: 2; SEQ ID NO: 8 and SEQ ID NO: 5; SEQ ID NO: 8, SEQ ID NO: 1, and SEQ ID NO: 2; SEQ ID NO: 8, SEQ ID NO: 1, and SEQ ID NO: 5; SEQ ID NO: 8, SEQ ID NO: 2, and SEQ ID NO: 5; or SEQ ID NO: 8, SEQ ID NO: 1, SEQ ID NO: 2, and SEQ ID NO: 5.

In some embodiments, the promoter is an inducible promoter. In some embodiments, the promoter is a tissue-specific promoter. In some embodiments, the promoter is a seed-specific promoter.

In some embodiments, the desiccation tolerance of the transgenic plant is increased by at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, or at least about 1000%, as compared to a plant not comprising the DNA construct.

In some embodiments, the plant is maize, bean, soybean, wheat, barley, hay, rice, peanut, cotton, tomato, cucurbit, okra, eggplant, pepper, sugar beet, sugarcane, cassava, potatoes, palm, rapeseed, sunflower, coconut, olive, flax, safflower, sesame, apple, pear, grape, strawberry, blackcurrant, redcurrant, gooseberry, guava, lucuma, chili pepper, pomegranate, kiwifruit, cranberry, blueberry, blackberry, raspberry, boysenberry, banana, plum, cherry, peach, apricot, mango, orange, lime, lemon, grapefruit, pineapple, fig, mulberry, hedge apple, osage-orange, or breadfruit.

Another aspect of the present disclosure provides a plant part of a transgenic plant described above.

Another aspect of the present disclosure provides an artificial DNA construct comprising, as operably associated components in the 5' to 3' direction of transcription: a promoter that functions in a plant; a polynucleotide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a sequence at least 95% identical thereto; and a transcriptional termination sequence.

Another aspect of the present disclosure provides a method of increasing desiccation tolerance of a plant comprising: transforming a plant with an artificial DNA construct comprising, as operably associated components in the 5' to 3' direction of transcription: a promoter that functions in a plant; a polynucleotide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a sequence at least 95% identical thereto; and a transcriptional termination sequence; wherein the transgenic plant has an increased desiccation tolerance, increased drought tolerance or increased water use efficiency. compared to a plant without the DNA construct.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 4A is an image of Northernblot analysis of overexpression lines of Phypa__169276 to WT. FIG. 4B is a pair of images depicting results from a desiccation assay in which tissues from 6-day-old WT, Δabi3 and Phypa__169276 overexpression lines to Δabi3 were treated with ABA (10 μM) for 24 hours. Tissues were dried for 30 hours, rehydrated with sterile distilled water, and incubated for 1 week.

FIG. 5A is an image of Northernblot analysis of overexpression lines of Phypa__169276 to A abi3. FIG. 5B is a pair of images depicting results from a desiccation assay in which tissues from 6-day-old WT, Δabi3 and Phypa__169276 overexpression lines to Δabi3 were treated with ABA (10 μM) for 24 hours. Tissues were dried for 48 hours, rehydrated with sterile distilled water, and incubated for 1 week.

DETAILED DESCRIPTION OF THE INVENTION

Figure 1:
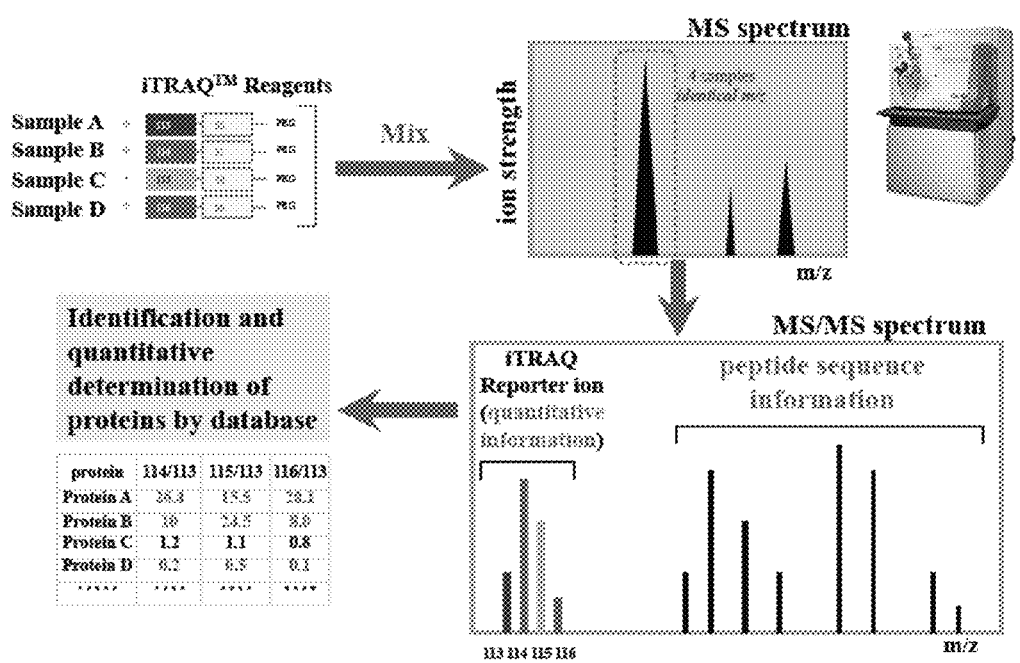
FIG. 1 is a series of charts and bar graphs providing a graphical overview of quantitative proteomic analysis using iTRAQ.

The present disclosure is based, at least in part, on the discovery of reduced desiccation tolerance of a moss line having a knock-out gene encoding a protein controlled by ABA and ABI3 during the desiccation-rehydration process. Such genes were identified according to quantitative proteomics analysis using iTRAQ (Isobaric Tags for Relative and Absolute Quantification) to reveal the regulatory network controlled by ABA and ABI3 during the desiccation-rehydration process. As described herein, from the thousands of proteins identified, close to one hundred were shown to increase more than two point five-fold with ABA treatment, and eight were shown to require both ABI3 and ABA. These results suggest that the gene regulatory pathway that requires both ABA and ABI3 control a relatively few proteins, and that these proteins can be used to increase desiccation tolerance, increase drought tolerance or increase water use efficiency in plant tissues.

ABA and ABI3 are generally discussed in Marella et al. 2006 The Plant Journal 46, 1032-1044; Khandelwal et al. 2010 Science 327, 546; and Yotsui et al. 2013 New Phytologist 199, 101-109. Desiccation tolerance in angiosperm seeds and in vegetative tissues of the moss *Physcomitrella patens* use similar regulatory pathways. The phytohormone abscisic acid (ABA) is a key controlling molecule that allows seeds to survive desiccation by activating a set of genes whose products presumably protect seed tissue to water loss. ABA acts through regulatory (transcription) factors such as ABSCISIC ACID INSENSITIVE 3 (ABI3). ABA and homologs of ABI3 are both found in *P. patens* and using a promoter active in wheat seed and linked to a reporter genes, it was found that ABA can activate this reporter gene in moss cells. Furthermore, one of three homologs of ABI3 found in *P. patens* partially complements the *Arabidopsis* abi3-6mutant. Both of these latter results indicate that the ABA signaling pathway exists in moss and that the regulatory components are similar. Thus, gene regulatory pathways that include both ABA and ABI3 originally evolved for cellular protection from water deficits but independently have been used to provide desiccation tolerance in normal tissues of bryophytes and in angiosperm seeds. For at least the above reasons, proteins controlled by ABA and ABI3 during the desiccation-rehydration process in moss can be employed in similar fashion in higher plants not containing such native proteins or expressing the same or similar proteins at lower levels or under different regulatory control.

According to an approach described herein, a plant can be transformed so as to express or overexpress a polypeptide responsive to ABA and requiring ABI3 so as to provide or increase tolerance or resistance to desiccation. For example, a plant can be transformed to express or overexpress one or more polypeptides encoded by SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof.

Proteins

As described herein, from the thousands of proteins identified in quantitative proteomics analysis using iTRAQ, eight were shown to require both ABI3 and ABA. Because the gene regulatory pathway that requires both ABA and ABI3 control a relatively few proteins, these proteins can be used to increase desiccation tolerance, increase drought tolerance or increase water use efficiency in plant tissues.

One aspect of the present disclosure provides a plant in which one or more proteins encoded by a transcribable nucleic acid molecule selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, are expressed or overexpressed in a plant so as to provide or increase desiccation tolerance, increase drought tolerance or increase water use efficiency. Such transcribable nucleic acid molecule(s) can be heterologous nucleotide sequences. A transcribable nucleic acid molecule of a heterologous construct can include a nucleic acid molecule that is already present in the host cell, a nucleic acid molecule from another organism, a nucleic acid molecule from a different organism, or a nucleic acid molecule generated externally, such as a nucleic acid molecule containing an antisense message of a gene, or a nucleic acid molecule encoding an artificial or modified version of a gene. A transcribable nucleic acid molecule can be any sequence encoding a polypeptide of interest. For example, a transcribable nucleic acid molecule can be a gene encoding a polypeptide having a particular activity of interest. A transcribable nucleic acid molecule can be gene selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof. Such transcribable nucleic acid molecule(s) can be incorporated into a construct for transformation of a plant according to conventional techniques.

For example, one or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, two or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, three or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, four or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, five or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, six or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, seven or more of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant. As another example, all of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a variant thereof, can be expressed or overexpressed in a plant.

A plant cell can be transformed with one or more heterologous nucleotide sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or a nucleotide sequence having at least about 90% sequence identity thereto, or a complementary sequence to any of these sequences, such that expression or overexpression of the encoded polypeptide provides or increases tolerance of desiccation or desiccation resistance. For example, a plant can be transformed with a nucleotide sequence having at least about 91%, at least about 92%, at least about 93%, at least about 94%, at least about 95%, at least about 96%, at least about 97%, at least about 98%, or at least about 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, such that expression or overexpression of the encoded polypeptide provides or increases tolerance of desiccation or desiccation resistance. Such transcribable sequences can be heterologous nucleotide sequences.

A plant can be transformed with an isolated polynucleotide that hybridizes to any of the above discussed nucleic acid sequences under stringent conditions thereto over the entire length of said sequence; said stringent conditions comprising incubation at 65° C. in a solution comprising 6×SSC (0.9 M sodium chloride and 0.09 M sodium citrate); and which encodes a polypeptide that when expressed or overexpressed in the plant provides or increases tolerance of desiccation or desiccation resistance.

Sequences for nucleotides referred to by Accession No. and Phypa ID can be obtained at, for example, the website cosmoss.org.

A transcribable nucleic acid molecule can be Accession No. gi168047556, Phypa ID 169276 or SEQ ID NO: 1, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi167999540, Phypa ID 112415 or SEQ ID NO: 2, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168052229, Phypa ID 27775 or SEQ ID NO: 3, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168049029, Phypa ID 194258 or SEQ ID NO: 4, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168000434, Phypa ID 113212 or SEQ ID NO: 5, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168038393, Phypa ID 190133 or SEQ ID NO: 6, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168002106, Phypa ID 159190 or SEQ ID NO: 7, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

A transcribable nucleic acid molecule can be Accession No. gi168015696, Phypa ID 122983 or SEQ ID NO: 8, or a nucleotide sequence having at least about 90%, at least about 91%, at least about 92%, at least about 93%, at least about 94%, at least about 95%, at least about 96%, at least about 97%, at least about 98%, or at least about 99% sequence identity thereto, such that expression or overexpression of the encoded polypeptide provides or increases desiccation tolerance.

Using targeted gene deletion techniques, deletion lines are developed for combinations of the four genes shown to require both ABI3 and ABA as follows: Accession No. gi168047556, Phypa ID 169276 (SEQ ID NO: 1); Accession No. gi167999540, Phypa ID 112415 (SEQ ID NO: 2); Accession No. gi168000434, Phypa ID 113212 (SEQ ID NO: 5); and Accession No. gi168015696, Phypa ID 122983 (SEQ ID NO: 8).

As shown herein, transcribable nucleic acid molecule having a sequence of Accession No. gi168015696, Phypa ID 122983 (SEQ ID NO: 8) was shown to be strongly associated with desiccation tolerance. As such, a transformed plant can be engineered with a transcribable nucleic acid molecule of SEQ ID NO: 8, or a variant thereof, so as to increase desiccation tolerance, increase drought tolerance or increase water use efficiency of the plant. Furthermore, in addition to SEQ ID NO: 8, or a variant thereof, a plant can be transformed with one or more additional transcribable nucleic acid molecules described herein. For example, a plant can be transformed with SEQ ID NO: 8, or a variant thereof, and at least one of SEQ ID NO: 1, SEQ ID NO: 2, SEQ ID NO: 3, SEQ ID NO: 4, SEQ ID NO: 5, SEQ ID NO: 6, or SEQ ID NO: 7, or a variant thereof. Exemplary combinations include, but are not limited to: SEQ ID NO: 8 and SEQ ID NO: 1; SEQ ID NO: 8 and SEQ ID NO: 2; SEQ ID NO: 8 and SEQ ID NO: 5; SEQ ID NO: 8, SEQ ID NO: 1, and SEQ ID NO: 2; SEQ ID NO: 8, SEQ ID NO: 1, and SEQ ID NO: 5; SEQ ID NO: 8, SEQ ID NO: 2, and SEQ ID NO: 5; SEQ ID NO: 8, SEQ ID NO: 1, SEQ ID NO: 2, and SEQ ID NO: 5. For example, a plant can be transformed with SEQ ID NO: 8, or a variant thereof, and SEQ ID NO: 1, or a variant thereof. One of ordinary skill will understand that plants transformed with other combinations of transcribable nucleic acid molecules described herein can be generated.

Constructs

Any of the transcribable polynucleotide molecule sequences described above can be provided in a construct. Constructs of the present disclosure generally include a promoter functional in the host plant operably linked to a transcribable polynucleotide molecule, such as provided in SEQ ID NO: 1, 3, 5, or 7, and variants thereof as discussed herein.

Exemplary promoters are discussed above. One or more additional promoters may also be provided in the recombinant construct. These promoters can be operably linked to any of the transcribable polynucleotide molecule sequences described herein.

In addition, constructs can include, but are not limited to, additional polynucleotide molecules from an untranslated region of the gene of interest. These additional polynucleotide molecules can be derived from a source that is native or heterologous with respect to the other elements present in the construct.

Promoters

A transcribable nucleic acid molecule encoding a polypeptide responsive to ABA and requiring ABI3 so as to provide or increase tolerance or resistance to desiccation can be operably linked to a promoter for transformation of a plant cell. The promoter can be any promoter functional in a plant cell (see e.g., Weise et al. Applied Microbiology and Biotechnology 70(3), 337-345; Saidi et al. 2005 Plant Molecular Biology 59(5), 697-711; Horstmann et al. 2004 BMC Biotechnology 4; Holtorf et al. 2002 Plant Cell Reports 21(4), 341-346; Zeidler et al. 1996 Plant Molecular Biology 30(1), 199-205). The promoter can be an inducible promoter.

The promoter can be any promoter endogenously associated with SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or analogs thereof in other species.

Examples of promoters than can be used in accord with methods and compositions described herein include, but are not limited to, ubiquitin promoter; factor EF1α gene promoter (see e.g., US App Pub No. 2008/0313776); rice tungro bacilliform virus (RTBV) gene promoter (see e.g., US App Pub No. 2008/0282431); cestrum yellow leaf curling virus (CmYLCV) promoter (see e.g., Stavolone et al. Plant Molecular Biology 53(5), 663-673); tCUP cryptic promoter system (see e.g., Malik et al. 2002 Theoretical and Applied Genetics 105(4), 505-514); T6P-3 promoter (see e.g., JP2002238564); S-adenosyl-L-methionine synthetase promoter (see e.g., WO/2000/037662); Raspberry E4 gene promoter (see e.g., U.S. Pat. No. 6,054,635); cauliflower mosaic virus 35S promoter (see e.g., Benfey et al. 1990 Science 250(4983), 959-966); figwort mosaic virus promoter (see e.g., U.S. Pat. No. 5,378,619); conditional heat-shock promoter (see e.g., Saidi et al. 2005 Plant Molecular Biology 59(5), 697-711); promoter subfragments of the sugar beet V-type H+-ATPase subunit c isoform (see e.g., Holtorf et al. 2002 Plant Cell Reports 21(4), 341-346); beta-tubulin promoter (see e.g., Jost et al. 2005 Current Genetics 47(2), 111-120); and bacterial quorum-sensing components (see e.g., You et al. 2006 Plant Physiology 140 (4), 1205-1212). For example, a promoter can be a heat-shock promoter. As another example, a promoter can be an inducible promoter providing for expression at germination or seedling stage.

A promoter can be a tissue specific promoter. For example, a transcribable nucleic acid molecule described herein can be operably linked to a pollen-, flower-, seed-, leaf-, or stem-specific promoter. As another example, a transcribable nucleic acid molecule described herein can be operably linked to a seed-specific promoter.

Inclusion of a termination region control sequence is optional, and if employed, then the choice is be primarily one of convenience, as the termination region is relatively interchangeable. The termination region may be native to the transcriptional initiation region (the promoter), may be native to the nucleic acid sequence of interest, or may be obtainable from another source.

A promoter of the present disclosure can be incorporated into a construct using marker genes as described and tested for an indication of gene expression in a stable host system. As used herein the term "marker gene" refers to any transcribable nucleic acid molecule whose expression can be screened for or scored in some way.

Plant

A plant or plant cell can be transformed with a construct including a transcribable nucleic acid molecule described herein operably linked to a promoter.

As used herein, the term "plant" can include plant cells, plant protoplasts, plant cells of tissue culture from which a plant can be regenerated, plant calli, plant clumps and plant cells that are intact in plants or parts of plants such as pollen, flowers, seeds, leaves, stems, and the like.

A host plant can be any plant in which it is desirable to increase desiccation tolerance, increase drought tolerance or increase water use efficiency. A host plant can be a flowering plant, conifer, fern or moss. A host plant can be angiosperm or a gymnosperm. A host plant can be monocot or a dicot. A host plant can be an agronomically important plant, such as maize (corn), bean, soybean, wheat, barley, hay (e.g., alfalfa and legume and grass mixtures), rice, peanut, cotton, tomato, cucurbit (e.g., squash, pumpkin, gourd, cucumber, melon, watermelon, zuchini), okra, eggplant, pepper, sugar beet, sugarcane, cassava, potatoes, palm, rapeseed (canola), sunflower, coconut, olive, flax, safflower, sesame, apple, pear, grape, strawberry, blackcurrant, redcurrant, gooseberry, guava, lucuma, chili pepper, pomegranate, kiwifruit, cranberry, blueberry, blackberry, raspberry, boysenberry, banana, plum, cherry, peach, apricot, mango, orange, lime, lemon, grapefruit, pineapple, fig, mulberry, hedge apple, osage-orange, or breadfruit.

A transformed plant or plant cell can be analyzed for the presence of a gene of interest and the expression level or profile conferred by the construct of the present disclosure. Those of skill in the art are aware of the numerous methods available for the analysis of transformed hosts. For example, methods for host analysis include, but are not limited to Southern blots or northern blots, PCR-based approaches, biochemical analyses, phenotypic screening methods, and immunodiagnostic assays.

Tolerance

Desiccation tolerance is generally understood as an ability of an organism to withstand or endure extreme dryness, or drought-like conditions, or the ability to continue a plant function (i.e., reduce strain, i.e., observed biological changes that occur in response to stress, i.e., an environmental condition that is capable of causing a biologically injurious change) despite reductions in plant water potential (see generally, Salisbury, Units, Symbols, and Terminology for Plant Physiology 1996 Oxford University Press, New York, ISBN019509445X). Desiccation tolerance is generally understood As described herein, desiccation tolerance in a plant can be provided or increased by engineering a plant to express or overexpress one or more polypeptides encoded by a transcribable nucleic acid molecule described herein (e.g., SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, or variants thereof).

Processes to assess desiccation tolerance of a plant are well known (see e.g. Jenks and Wood 2007 Plant Desiccation Tolerance, 340 p., Wiley-Blackwell, ISBN 978-0-8138-1263-2; Luttge et al. 2011 Plant Desiccation Tolerance, Ecological Studies, Vol. 215, 386 p., Springer, ISBN 978-3-642-19105-3; Khandelwal et al. 2010 Science 327: 546. Except as otherwise noted herein, therefore, assessing desiccation tolerance of a plant can be carried out in accordance with such processes. For example, desiccation tolerance can be assessed according to survival or growth rate during or after dehydration/rehydration cycles (see e.g., Example 6, Example 7).

A plant transformed with one or more transcribable nucleic acid molecules described herein can exhibit increased desiccation tolerance. For example, a plant transformed with one or more transcribable nucleic acid molecules described herein can exhibit at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1000%, or more, increased desiccation tolerance as compared to a non-transformed control plant of the same or similar type.

Drought tolerance is understood to be an ability of a plant to survive or yield under drought conditions despite lack of available soil water to meet its maximal needs (see generally, Salisbury, Units, Symbols, and Terminology for Plant Physiology 1996 Oxford University Press, New York, ISBN019509445X). Drought conditions are understood to be a generally insufficient availability of soil water on a meso- or macro-environmental scale to supply the maximal requirements of otherwise well-adapted plants (see generally, Salisbury, Units, Symbols, and Terminology for Plant Physiology 1996 Oxford University Press, New York, ISBN019509445X). Processes to assess drought tolerance of a plant are well known (see generally, Werner et al. 1991 Planta 186, 99-103). Except as otherwise noted herein, therefore, assessing drought tolerance of a plant can be carried out in accordance with such processes.

A plant transformed with one or more transcribable nucleic acid molecules described herein can exhibit increased drought tolerance. For example, a plant transformed with one or more transcribable nucleic acid molecules described herein can exhibit at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1000%, or more, increased drought tolerance as compared to a non-transformed control plant of the same or similar type.

Water use efficiency is understood to be a comparative measure of plant productivity per unit water used (see generally, Salisbury, Units, Symbols, and Terminology for Plant Physiology 1996 Oxford University Press, New York, ISBN019509445X). Agricultural water use efficiency can be defined for a growing season either as yield per unit irrigation water applied or biomass produced per unit of transpiration. Instantaneous physiological water use efficiency can be defined as moles of carbon dioxide fixed by photosynthesis per mole of water transpired. Processes to assess water use efficiency (e.g., agricultural water use efficiency or instantaneous physiological water use efficiency) of a plant are well known (e.g., LI-6400XT Portable Photosynthesis System, LI-COR Biosciences). Except as otherwise noted herein, therefore, assessing water use efficiency of a plant can be carried out in accordance with such processes.

A plant transformed with one or more transcribable nucleic acid molecules described herein can exhibit increased water use efficiency (e.g., agricultural water use efficiency or instantaneous physiological water use efficiency). For example, a plant transformed with one or more transcribable nucleic acid molecules described herein can exhibit at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, at least about 1000%, or more, increased water use efficiency (e.g., agricultural water use efficiency or instantaneous physiological water use efficiency) as compared to a non-transformed control plant of the same or similar type.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST™, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$ (fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem. Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™

RNAi Designer, Invitrogen; siRNA Whitehead Institute Design Tools, Bioinoformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Mass Spectrometric Analysis

Nano LC-MS/MS analyses were performed on an LTQ-Orbitrap XL (Thermo Fisher Scientific, Waltham, Mass., USA) equipped with a nano-ESI source and coupled to a Paradigm MG4 pump (MichromBioresources, Auburn, Calif., USA) and autosampler (HTC PAL, CTC Analytics, Zwingen, Switzerland). Peptide mixtures were separated on MagicC18AQ column (100 mm×150 mm, 3.0 mm particle size, 300 Å, MichromBioresources, Auburn, Calif., USA)

with a flow rate of 500 nl/min. Linear gradient of 5-35% buffer B in buffer A for 150 min, 30-95% buffer B in buffer A for 4 min, and 95% buffer B and 5% buffer A for 5 min and finally decreased to 5% buffer B in buffer A was employed (buffer A=0.1% formic acid in 2% acetonitrile, buffer B=0.1% formic acid in 90% acetonitrile). Up to three CID and HCD spectra were acquired in a data-dependent acquisition mode following each full scan (m/z, 400-1,500).

Example 2 iTRAQ

The following example describes quantitative proteomics analysis using iTRAQ (Isobaric Tags for Relative and Absolute Quantification) to reveal the regulatory network controlled by ABA and ABI3 during the desiccation-rehydration process. A graphical overview of the proteomic analysis using iTRAQ is provided in FIG. 1.

Figure 2:
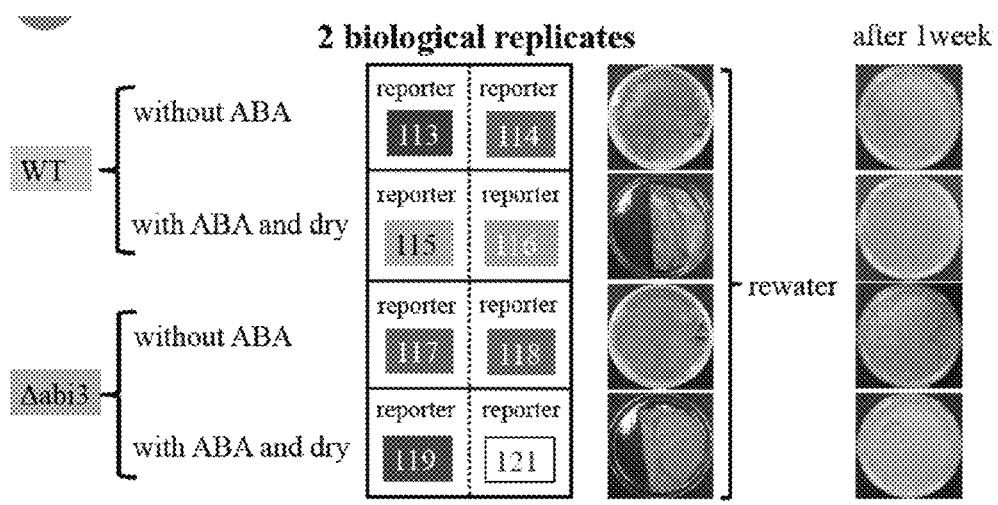
FIG. 2 is a chart providing an overview of sample preparation for iTRAQ analysis.

The frozen *Physcomitrella* protonemata samples were crushed to frozen powder with a Multi-Beads Shocker. The frozen powder was then treated with urea lysis buffer (7 M urea, 2 M thiourea, 4% CHAPS, 1× protease inhibitor cocktail and 1× phosphatase inhibitor cocktail). After centrifugation at 13,200 rpm for 15 min, the supernatant was recovered and stored at −85° C. until use. Protein concentrations were determined with the RC-DC Protein Assay kit, using BSA as the concentration standard. A graphical overview of sample preparation for iTRAQ analysis is provided in FIG. 2.

Extracted proteins were purified by using 2D-clean up kit. Subsequently, 100 μg of each protein were dissolved in 10 μl of 7 M urea, 2 M Thiourea, 4% CHAPS and 20 μl of 1M TEAB pH8.5, reduced, alkylated and digested with trypsin according to the manufacturer's protocol. Trypsin-digested peptides were concentrated to 30 μl by a centrifugal concentrator. Samples were labeled with the iTRAQ reagent according to the manufacturer's protocol. WT without ABA was labeled with iTRAQ reagent 113 and 114, WT with ABA and dry was labeled with 115 and 116, Δabi3 without ABA was labeled with 117 and 118, Δabi3 with ABA and dry was labeled with 119 and 121. The labeled peptide samples were then pooled and desalted with Sep-Pak Light C18 Cartridges and peptides were dried in a centrifugal prior to strong cation exchange (SCX) fractionation.

iTRAQ Data Analysis.

Protein identification and quantification for iTRAQ analysis was carried out using Proteome Discoverer software (v. 1.1) (Thermo Fisher Scientific) against NCBInr database. The MS/MS data were investigated only against the *Physcomitrella patens*. Search parameters for peptide and MS/MS mass tolerance were 10 ppm and 0.8 Da, respectively, with allowance for two missed cleavages made from the trypsin digest. Carbamidomethylation (Cys) and iTRAQ8plex (Lys, N-terminal) were specified as static modifications, whereas iTRAQ8plex (Tyr), and oxidation (Met) were specified as variable modifications in the database search. The false discovery rate of 1% was calculated by Proteome Discoverer based on a search against a corresponding randomized database. Relative protein abundances were calculated using the ratio of iTRAQ reporter ion in the MS/MS scan.

Example 3

Identification of ABA Responsible Proteins in WT and Δabi3

Protein identification and quantification for iTRAQ analysis was carried out using Proteome Discoverer software (ver.1.1) (Thermo Fisher Scientific) against NCBInr database. The MS/MS data were investigated only against the *P. patens*. Also compared were proteins identified by iTRAQ analysis with mRNAs identified by microarray analysis. Also confirmed was expression of mRNA codes proteins identified with a significant change both WT and Δabi3.

Results of iTRAQ analysis identified a total of 3582 proteins as being ABA responsive, with a false discovery rate (FDR) of less than 1%. A subset of 98 proteins from this group, including 19 LEA proteins, were increased more than two point five-fold with ABA treatment (see e.g., TABLE 1). The ABA responsible proteins could be sorted into nine categories according to their biological function as described by EMBL-EBI. These categories include seed maturation (19.39%), defense (9.18%), metabolism (16.33%), protein synthesis (2.04%), ion transport (2.04%), transcription (3.06%), unclassified (7.14%), unknown moss specific (21.43%) and unknown (19.39%).

Sequences for nucleotides referred to by Accession No. and Phypa ID can be obtained at, for example, the website cosmoss.org.

Eight proteins were identified as having a significant change between WT and Δabi3 with ABA and desiccation, which are encoded by the ORF regions of the following nucleotide sequences: Accession No. gi168047556, Phypa ID 169276 (SEQ ID NO: 1); Accession No. gi167999540, Phypa ID 112415 (SEQ ID NO: 2); Accession No. gi168052229, Phypa ID 27775 (SEQ ID NO: 3); Accession No. gi168049029, Phypa ID 194258 (SEQ ID NO: 4); Accession No. gi168000434, Phypa ID 113212 (SEQ ID NO: 5); Accession No. gi168038393, Phypa ID 190133 (SEQ ID NO: 6); Accession No. gi168002106, Phypa ID 159190 (SEQ ID NO: 7); and Accession No. gi168015696, Phypa ID 122983 (SEQ ID NO: 8).

Only four proteins required both ABI3 and ABA: Accession No. gi168047556, Phypa ID 169276 (SEQ ID NO: 1); Accession No. gi167999540, Phypa ID 112415 (SEQ ID NO: 2); Accession No. gi168000434, Phypa ID 113212 (SEQ ID NO: 5); and Accession No. gi168015696, Phypa ID 122983 (SEQ ID NO: 8).

TABLE 1

Protein identification and quantification for iTRAQ analysis was carried out using Proteome Discoverer software (ver.1.1) (Thermo Fisher Scientific) against NCBInr database. The MS/MS data were investigated only against the *P. patens*. Double lines show proteins identified with a significant change between WT and Δabi3 with ABA and desiccation by iTRAQ analysis. Blue letters shows proteins were increased more than two point five-fold with ABA treatment.

| | | | | | Up-regulation folds with ABA and dry (iTRAQ) | | | | WT with ABA | microarray Fold change [Δ0] vs [WT0] | [Δ24] vs [WT24] |
|---|---|---|---|---|---|---|---|---|---|---|---|
| Accession | Phypa ID | annotation | Coverage | #peptides | [WT]1 | [WT]2 | [Δabi3]1 | [Δabi3]2 | | | |
| Seed maturation | | | | | | | | | | | |
| gi168347838 | 169526 | LATE EMBRYOGENESIS ABUNDANT RELATED | 9.74 | 4 | 5.882 | 12.767 | 1.304 | 1.140 | 1541.92 | −1.93 | −58.14 |
| gi168701480 | 132415 | Small hydrophilic plant seed protein | 45.98 | 6 | 2.543 | 3.445 | 1.042 | 0.703 | 38977.95 | 1.01 | −4.11 |
| gi167997373 | 110912 | Late embryogenesis abundant protein (LEA) family protein | 34.69 | 19 | 11.652 | 20.860 | 39.883 | 8.981 | 125.78 | −3.12 | −2.47 |
| gi168034736 | 166566 | late embryogenesis abundant domain-containing protein/LEA domain-containing protein | 32.63 | 14 | 8.804 | 18.853 | 30.765 | 4.071 | 18.70 | −42.82 | −2.11 |
| gi168042734 | 140531 | Seed maturation protein | 30.54 | 25 | 7.144 | 11.457 | 7.383 | 3.522 | 1013.14 | 1.63 | −1.48 |
| gi168020025 | 34885 | Late embryogenesis abundant protein (LEA) family protein | 59.78 | 26 | 7.066 | 11.882 | 20.671 | 8.355 | 53.70 | −1.26 | −1.08 |
| gi168025625 | 233250 | late embryogenesis abundant domain-containing protein/LEA domain-containing protein | 39.25 | 60 | 6.363 | 11.633 | 6.322 | 3.023 | 47.79 | −27.74 | −2.56 |
| gi168058121 | 53626 | late embryogenesis abundant domain-containing protein/LEA domain-containing protein | 51.32 | 12 | 8.133 | 10.262 | 6.884 | 4.241 | 59.03 | −2.37 | −3.85 |
| gi168055759 | 223670 | late embryogenesis abundant domain-containing protein/LEA domain-containing protein | 48.22 | 19 | 8.105 | 8.266 | 6.569 | 3.388 | 99.49 | −3.93 | −4.98 |
| gi168033892 | 166392 | late embryogenesis abundant domain-containing protein/LEA domain-containing protein | 35.59 | 67 | 6.048 | 8.486 | 4.787 | 2.683 | 139.48 | −38.50 | −3.69 |
| gi168066331 | 173331 | Dehydrin family protein | 36.21 | 25 | 5.745 | 8.388 | 11.005 | 3.498 | 16.60 | 1.27 | −1.29 |
| gi168063969 | 153020 | Phypa_459381 mRNA sequence for Late embryogenesis abundant protein, group 3 (LEA) [*Zea mays*] | 22.03 | 6 | 5.503 | 8.335 | 7.841 | 2.530 | 48.37 | −1.53 | −1.98 |
| gi168058168 | 171483 | LATE EMBRYOGENESIS ABUNDANT (PLANTS) LEA-RELATED | 14.47 | 13 | 5.063 | 8.277 | 12.739 | 5.634 | 3.25 | 1.54 | 1.34 |
| gi168065609 | 154342 | late embryogenesis abundant domain-containing protein, putative/LEA protein, putative | 26.48 | 12 | 4.235 | 3.092 | 4.757 | 2.627 | 29.53 | −2.92 | −3.65 |
| gi168063809 | 152915 | late embryogenesis abundant domain-containing protein/LEA domain-containing protein | 59.71 | 23 | 3.897 | 6.431 | 5.241 | 2.437 | 566.05 | −8.83 | −4.09 |
| gi168005886 | 25919 | late embryogenesis abundant domain-containing protein, putative/LEA protein, putative | 24.32 | 11 | 3.898 | 6.474 | 4.586 | 2.232 | 41.62 | −1.18 | −1.98 |
| gi38176433 | 221321 | Dehydrin Hoe | 47.29 | 45 | 3.229 | 4.896 | 4.857 | 2.642 | 3414.72 | −9.57 | −14.00 |
| gi168063260 | 172612 | late embryogenesis abundant protein | 35.16 | 36 | 3.198 | 5.858 | 7.317 | 3.886 | 1.91 | −1.68 | 1.23 |
| gi167997371 | 64056 | Late embryogenesis abundant (LEA) protein | 12.9 | 7 | 2.785 | 4.972 | 5.271 | 2.113 | | | |
| Defense | | | | | | | | | | | |
| gi168352229 | 97425 | Cysteine-rich secretary protein Family | 11.03 | 2 | 11.242 | 16.993 | 5.382 | 3.260 | 844.05 | −2.05 | −6.88 |
| gi168049639 | 193258 | LANC-LIKE PROTEIN | 1.52 | 1 | 7.648 | 13.508 | 3.565 | 1.965 | 49.86 | 1.13 | −2.35 |

TABLE 1-continued

Protein identification and quantification for iTRAQ analysis was carried out using Proteome Discoverer software (ver.1.1) (Thermo Fisher Scientific) against NCBInr database. The MS/MS data were investigated only against the *P. patens*. Double lines show proteins identified with a significant change between WT and Δabi3 with ABA and desiccation by iTRAQ analysis. Blue letters shows proteins were increased more than two point five-fold with ABA treatment.

| Accession | Phypa ID | annotation | Coverage | #peptides | iTRAQ Up-regulation folds with ABA and dry | | | | | WT with ABA | microarray Fold change | | |
|---|---|---|---|---|---|---|---|---|---|---|---|---|---|
| | | | | | [WT]1 | [WT]2 | [Δabi3]1 | [Δabi3]2 | | | [Δ0] vs [A0] | [WT0] | [Δ24] vs [WT24] |
| gi165001128 | 65913 | Hsp20/alpha crystallin family/SMALL HEAT-SHOCK PROTEIN (HSP20) FAMILY | 5.23 | 2 | 4.383 | 4.436 | 2.500 | 1.287 | — | — | — | — |
| gi117557347 | 114091 | CALCIUM-DEPENDENT LIPID-BINDING PROTEIN (CALB RELATED) | 5.76 | 6 | 7.369 | 10.927 | 8.478 | 5.718 | 48.53 | −1.00 | −1.53 |
| gi168053997 | 147280 | ASPARAGINE SYNTHETASE | 6.43 | 3 | 2.348 | 10.608 | 7.725 | 5.489 | −1.05 | −1.85 | −1.99 |
| gi168031730 | 166082 | AWPM-19-like family | 14.37 | 10 | 6.455 | 10.595 | 8.875 | 4.396 | 42.12 | 1.28 | 1.06 |
| gi168038266 | 217333 | 14-3-3 protein | 31.13 | 40 | 2.993 | 4.898 | 6.656 | 3.678 | 14.41 | 1.18 | 1.26 |
| gi69010337 | 161093 | NITROGEN METABOLIC REGULATION PROTEIN NMR-RELATED | 28.63 | 31 | 2.781 | 5.180 | 8.105 | 2.463 | 7.78 | 1.52 | 1.38 |
| gi165033788 | 83561 | proton gradient regulation 5 | 31.08 | 4 | 2.749 | 5.233 | 4.524 | 2.894 | −1.88 | −1.49 | −1.23 |
| gi168020452 | 125936 | Caleosin related protein | 10.62 | 4 | 2.739 | 4.181 | 3.743 | 3.636 | 40756.19 | −1.23 | −17.78 |
| Metabolism | | | | | | | | | | | | |
| | | SHORT-CHAIN DEHYDROGENASES/REDUCTASE | 5.54 | 4 | 48.871 | 66.814 | 1.849 | 2.140 | 5731.04 | −11.86 | −600.71 |
| | | ALDO/KETO REDUCTASE | 18.59 | 9 | 6.070 | 8.439 | 1.407 | 0.962 | 1780.14 | −4.26 | −68.22 |
| gi168023967 | 127465 | ALCOHOL DEHYDROGENASE RELATED | 6.15 | 10 | 9.977 | 16.928 | 6.469 | 2.861 | 3671.93 | −4.43 | −21.87 |
| gi168021556 | 210293 | Phosphaenolpyruvate carboxykinase | 9.31 | 11 | 3.656 | 5.632 | 2.738 | 0.960 | −1.17 | −2.03 | −1.06 |
| gi168002724 | 202843 | C-terminal domain of 1-Cys peroxidedoxin/PEROXIREDOXIN | 40.72 | 18 | 7.327 | 10.990 | 4.973 | 1.661 | 250.33 | −4.79 | −17.88 |
| gi168059949 | 150414 | INORGANIC PYROPHOSPHATASE | 11.59 | 6 | 6.851 | 10.058 | 7.487 | 4.838 | — | — | — |
| gi168018523 | 124664 | ZINC FINGER FIVE DOMAIN CONTAINING PROTEIN | 14.46 | 15 | 6.693 | 8.366 | 7.938 | 4.187 | 87.36 | 1.46 | −1.47 |
| gi167999436 | 158682 | LysM domain contain protein | 11.55 | 16 | 4.829 | 6.897 | 5.989 | 3.608 | 73.53 | 1.30 | −1.33 |
| gi168008176 | 205052 | ALDO/KETO REDUCTASE | 22.12 | 16 | 3.970 | 5.988 | 4.740 | 2.289 | 25.81 | 1.26 | −1.34 |
| gi168057984 | 197372 | CATALASE | 15.64 | 20 | 3.746 | 4.530 | 3.893 | 2.046 | 1107.08 | −2.88 | −2.04 |
| gi168003088 | 25822 | GRAM domain family protein | 11.6 | 7 | 3.538 | 6.055 | 5.397 | 1.956 | 3.09 | −1.33 | −1.28 |
| gi168032507 | 214778 | AMINOHYDROLASE | 3.97 | 5 | 3.278 | 4.835 | 4.337 | 1.640 | 3.35 | −1.35 | −1.74 |
| gi168016771 | 123644 | ALCOHOL DEHYDROGENASE RELATED | 2.4 | 3 | 3.132 | 4.553 | 2.938 | 1.046 | 4.73 | 1.01 | −2.35 |
| gi168015766 | 49632 | GLUTAREDOXIN | 7.07 | 2 | 3.025 | 4.597 | 3.055 | 1.709 | 67.93 | 1.37 | −1.44 |
| gi168029940 | 213846 | PHOSPHOLIPASE D | 9.81 | 10 | 2.755 | 3.331 | 3.538 | 2.389 | 7.22 | 1.86 | 1.36 |
| gi168006265 | 176782 | CARBOXYLASE:PYRUVATE/ACETYL-COA/PROPIONYL-COA | 5.42 | 5 | 2.705 | 3.899 | 4.289 | 1.089 | 1.41 | −1.89 | −1.84 |
| gi168059614 | 150204 | IRON-SULFUR DOMAIN CONTAINING PROTEIN | 5.06 | 6 | 2.509 | 3.837 | 2.440 | 1.013 | 1.09 | −1.36 | −1.25 |
| gi168046840 | 193394 | SHORT-CHAIN DEHYDROGENASES/REDUCTASE | 10.59 | 4 | 2.501 | 3.485 | 2.039 | 1.485 | 4.56 | 2.09 | 1.34 |
| Protein synthesis/fate | | | | | | | | | | | | |
| gi168055678 | 2950 | ALPHA/BETA HYDROLASE RELATED | 6.42 | 3 | 6.683 | 10.643 | 7.782 | 5.336 | 22.62 | 2.16 | −1.12 |
| gi168029624 | 213747 | Thioredoxin-like protein | 12.87 | 9 | 5.509 | 11.244 | 11.237 | 4.390 | 13.29 | −1.13 | −1.58 |
| gi168061135 | 198530 | Ribosomal protein L14 | 41.04 | 10 | 3.323 | 5.528 | 7.645 | 3.892 | 1.03 | 1.10 | 1.12 |
| gi168035968 | 136081 | Ribosomal protein L6 | 16.09 | 9 | 3.037 | 5.487 | 6.332 | 3.307 | — | — | — |
| Transport | | | | | | | | | | | | |

TABLE 1-continued

Protein identification and quantification for iTRAQ analysis was carried out using Proteome Discoverer software (ver.1.1) (Thermo Fisher Scientific) against NCBInr database. The MS/MS data were investigated only against the *P. patens*. Double lines show proteins identified with a significant change between WT and Δabi3 with ABA and desiccation by iTRAQ analysis. Blue letters shows proteins were increased more than two point five-fold with ABA treatment.

| Accession | Phypa ID | annotation | Coverage | #peptides | iTRAQ Up-regulation folds with ABA and dry [WT]1 | [WT]2 | [Δabi3]1 | [Δabi3]2 | WT with ABA | microarray Fold change [Δ0] vs [WT0] | [Δ24] vs [WT24] |
|---|---|---|---|---|---|---|---|---|---|---|---|
| gi168022840 | 77363 | MYOSIN-VII | 1.32 | 8 | 10.266 | 17.875 | 13.708 | 5.168 | — | — | — |
| gi167998408 | 111412 | Calcium-activated chloride channel | 2.55 | 4 | 6.062 | 9.280 | 8.310 | 4.149 | 180.85 | 1.51 | -1.46 |
| gi168065723 | 110643 | TRANSLOCASE OF INNER MITOCHONDRIAL MEMBRANE TIM22 | 42.86 | 11 | 3.329 | 2.934 | 4.831 | 2.851 | 19.87 | 1.45 | 1.23 |
| gi168020639 | 163517 | COPPER TRANSPORT PROTEIN ATOX1-RELATED | 5.26 | 1 | 3.367 | 4.432 | 4.658 | 2.993 | 4.68 | 1.43 | 1.18 |
| gi168045663 | 168786 | NAD DEPENDENT EPIMERASE/DEHYDRATASE | 18.46 | 31 | 2.539 | 4.638 | 3.623 | 2.435 | 9.54 | -1.27 | -1.46 |
| Signal transduction and regulation of transcription | | | | | | | | | | | |
| gi168058456 | 171520 | AP2 domain contain protein | 2.42 | 1 | 3.175 | 2.725 | 1.409 | 0.734 | — | — | — |
| gi168011320 | 178765 | TRANSFORMING GROWTH FACTOR INDUCED PROTEIN | 11.45 | 2 | 4.706 | 2.109 | 6.835 | 2.499 | 5260.38 | -24.95 | -20.38 |
| gi168049682 | 144692 | EF hand-containing protein | 16.05 | 9 | 4.898 | 6.011 | 3.887 | 2.639 | 37.80 | 1.27 | -1.33 |
| gi168003523 | 159544 | TRANSCRIPTIONAL REPRESSOR PROTEIN YY | 3.14 | 10 | 3.366 | 2.668 | 2.686 | 3.787 | 1.16 | -1.70 | -1.68 |
| gi168048824 | 91567 | SIN3B-RELATED | 1.8 | 9 | 3.664 | 4.632 | 3.698 | 2.285 | — | — | — |
| Unclassified | | | | | | | | | | | |
| gi168004061 | 67470 | Viral A-type inclusion protein repeat | 27.67 | 68 | 8.707 | 14.363 | 3.385 | 2.826 | 1241.23 | -8.83 | -40.02 |
| gi168002515 | 159259 | EFSD domain-containing protein | 3.61 | 10 | 7.558 | 11.857 | 8.100 | 6.675 | -1.43 | -1.15 | -1.18 |
| gi168058093 | 171446 | MITOCHONDRIAL CARRIER PROTEIN RELATED | 14.19 | 16 | 5.253 | 3.537 | 8.016 | 5.396 | 7.14 | 1.05 | -1.41 |
| gi168068011 | 173681 | SOUL heme-binding family protein | 11.61 | 5 | 2.861 | 4.963 | 3.141 | 1.917 | 8.71 | -1.09 | -1.30 |
| gi167999364 | 24243 | DNA repair ATPase-related | 16.92 | 11 | 2.873 | 4.448 | 3.835 | 1.176 | 5.79 | 1.11 | -1.20 |
| Unknown moss specific | | | | | | | | | | | |
| gi168003106 | 189190 | there are no functional annotations for this locus | 21.36 | 8 | 17.953 | 36.378 | 2.598 | 1.611 | 1444.27 | -13.06 | -122.71 |
| gi168051653 | 170187 | there are no functional annotations for this locus | 13.18 | 15 | 10.449 | 22.863 | 8.953 | 2.543 | 290.94 | -85.68 | -108.25 |
| gi168008551 | 160757 | there are no functional annotations for this locus | 19.73 | 9 | 5.398 | 8.476 | 3.107 | 1.380 | 6145.67 | -1.44 | -54.04 |
| gi168059789 | 96882 | there are no functional annotations for this locus | 3.2 | 3 | 3.539 | 5.337 | 1.968 | 1.223 | — | — | — |
| gi168007348 | 69345 | there are no functional annotations for this locus | 21.02 | 13 | 14.460 | 22.863 | 9.253 | 5.506 | 2842.01 | -2.79 | -11.70 |
| gi168057763 | 171387 | there are no functional annotations for this locus | 38.72 | 60 | 11.339 | 22.695 | 12.358 | 4.991 | 522.28 | 1.18 | -1.94 |
| gi168012482 | 161636 | there are no functional annotations for this locus | 43.14 | 71 | 9.932 | 39.421 | 18.834 | 5.523 | 240.83 | -43.67 | -28.37 |
| gi168010327 | 70813 | there are no functional annotations for this locus | 13.74 | 2 | 9.891 | 19.845 | 9.793 | 5.527 | — | — | — |
| gi168057767 | 171388 | there are no functional annotations for this locus | 34.18 | 24 | 6.623 | 9.543 | 6.791 | 3.823 | 25.07 | 2.22 | -1.32 |
| gi168008419 | 160688 | there are no functional annotations for this locus | 22.9 | 10 | 6.769 | 33.766 | 11.196 | 3.456 | 8379.37 | -4.08 | -4.54 |
| gi168024980 | 229196 | there are no functional annotations for this locus | 12.75 | 11 | 5.871 | 8.356 | 3.917 | 2.055 | 744.02 | -2.72 | -38.98 |
| gi168039669 | 232091 | there are no functional annotations for this locus | 11.4 | 10 | 4.773 | 8.798 | 31.42 | 2.210 | 1357.51 | -2.94 | -4.95 |
| gi168041604 | 87717 | there are no functional annotations for this locus | 6.89 | 4 | 4.240 | 7.736 | 4.123 | 1.724 | — | — | — |
| gi168033047 | 233882 | there are no functional annotations for this locus | 20.55 | 6 | 3.766 | 6.352 | 13.538 | 4.122 | 204.00 | -1.43 | -1.33 |
| gi167998520 | 64336 | there are no functional annotations for this locus | 17.25 | 21 | 3.375 | 4.705 | 2.678 | 3.358 | 116.59 | 1.86 | 1.21 |
| gi168053822 | 99184 | there are no functional annotations for this locus | 6.96 | 1 | 3.297 | 5.506 | 4.099 | 1.866 | — | — | — |

TABLE 1-continued

Protein identification and quantification for iTRAQ analysis was carried out using Proteome Discoverer software (ver.1.1) (Thermo Fisher Scientific) against NCBInr database. The MS/MS data were investigated only against the *P. patens*. Double lines show proteins identified with a significant change between WT and Δabi3 with ABA and desiccation by iTRAQ analysis. Blue letters shows proteins were increased more than two point five-fold with ABA treatment.

| Accession | Phypa ID | annotation | Coverage | #peptides | iTRAQ Up-regulation folds with ABA and dry | | | | | WT with ABA | microarray Fold change [A0] vs [WT0] | [A24] vs [WT24] |
|---|---|---|---|---|---|---|---|---|---|---|---|---|
| | | | | | [WT]1 | [WT]2 | [Δabi3]1 | [Δabi3]2 | | | | |
| gi168066383 | 173340 | there are no functional annotations for this locus | 43.15 | 99 | 3.367 | 4.891 | 5.914 | 2.746 | 67.40 | -1.17 | -1.39 |
| gi168004453 | 159758 | there are no functional annotations for this locus | 6.44 | 9 | 2.943 | 4.315 | 4.528 | 2.315 | 3548.78 | -1.90 | -2.35 |
| gi168052182 | 170304 | there are no functional annotations for this locus | 15.38 | 18 | 2.928 | 5.398 | 5.494 | 2.943 | 157.33 | -1.11 | -1.57 |
| gi168019178 | 163180 | there are no functional annotations for this locus | 19.23 | 5 | 2.773 | 4.078 | 3.657 | 3.082 | 2.51 | 1.91 | 1.66 |
| gi168041447 | 87628 | there are no functional annotations for this locus | 2.09 | 4 | 2.659 | 4.285 | 3.595 | 3.712 | — | — | — |
| Unknown | | | | | | | | | | | |
| gi168018696 | 122983 | there are no functional annotations for this locus | 30.41 | 18 | 15.344 | 23.949 | 1.718 | 1.459 | 304.25 | -1.38 | -7.69 |
| gi167999378 | 64955 | unknown | 4.91 | 3 | 6.898 | 8.994 | 2.643 | 5.668 | — | — | — |
| gi168003483 | 159520 | there are no functional annotations for this locus | 35.48 | 34 | 8.882 | 11.253 | 9.372 | 5.286 | 73.72 | -5.87 | -1.86 |
| gi168044535 | 168559 | Protein of unknown function (DUF1253) | 2.53 | 4 | 5.140 | 8.104 | 3.588 | 1.886 | 1.09 | 1.11 | 1.16 |
| gi168040629 | 167699 | Protein of unknown function (DUF567) | 21.43 | 15 | 4.223 | 5.449 | 8.505 | 3.811 | 9.15 | 1.35 | 1.01 |
| gi168039405 | 107294 | Protein of unknown function (DUF567) | 24.24 | 16 | 4.024 | 4.405 | 3.956 | 2.356 | 196.52 | -1.07 | -1.29 |
| gi167999195 | 64697 | there are no functional annotations for this locus | 6.5 | 4 | 3.863 | 8.858 | 9.538 | 4.495 | — | — | — |
| gi168052628 | 93565 | unknown | 6.42 | 4 | 3.590 | 4.859 | 3.938 | 2.119 | 1.34 | 1.02 | -1.02 |
| gi168036875 | 189292 | there are no functional annotations for this locus | 11.36 | 6 | 3.588 | 5.008 | 5.917 | 3.670 | 161.37 | 1.61 | -1.59 |
| gi168064705 | 99618 | unknown | 4.47 | 7 | 3.363 | 4.287 | 3.749 | 1.972 | — | — | — |
| gi168046560 | 235391 | unknown | 24 | 24 | 2.781 | 3.119 | 4.376 | 2.128 | 3290.74 | -4.37 | -4.47 |

Example 4

Analysis OF mRNA Expression

Northern blot analysis of mRNA expression was conducted for the eight genes (Accession No. gi168047556, Phypa ID 169276; Accession No. gi167999540, Phypa ID 112415; Accession No. gi168049029, Phypa ID 194258; Accession No. gi168000434, Phypa ID 113212; Accession No. gi168038393, Phypa ID 190133; Accession No. gi168002106, Phypa ID 159190; Accession No. gi168015696, Phypa ID 122983; and Accession No. gi168052229, Phypa ID 27775) significantly changed between WT and A abi3 with ABA and desiccation treatment.

Figure 3:
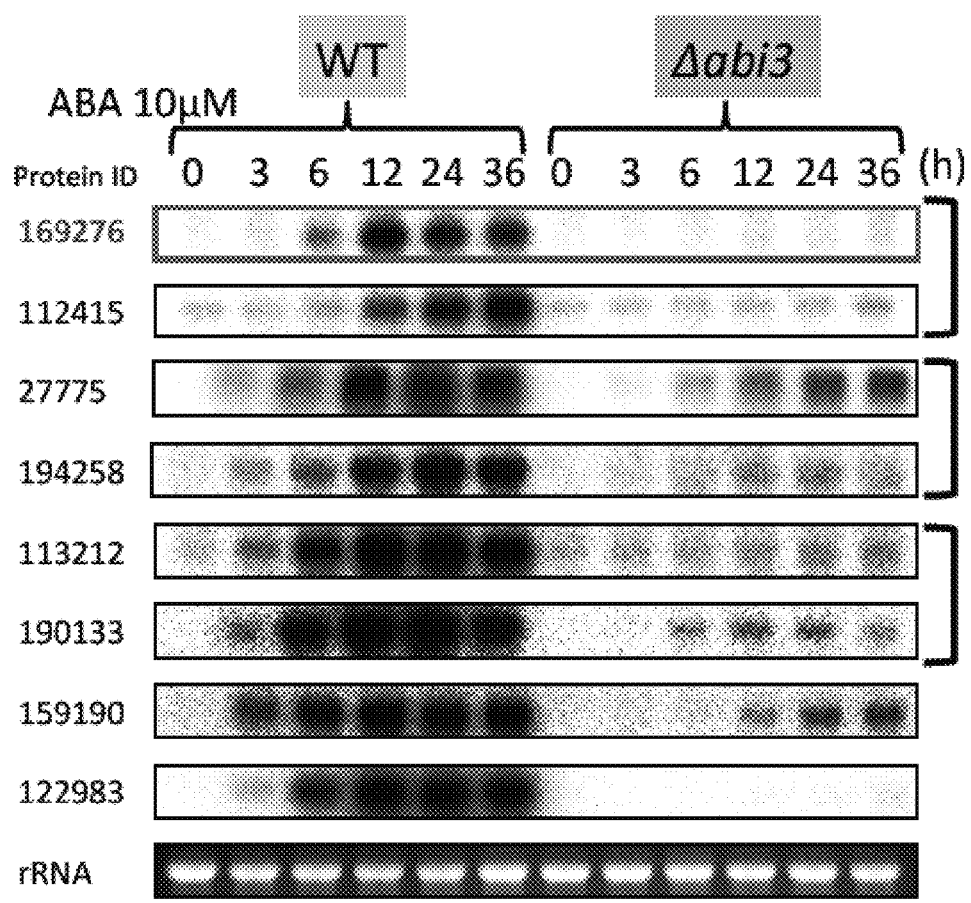
FIG. 3 is a series of images depicting Northern blot analysis of mRNA expression for the following genes: Accession No. gi168047556, Phypa ID 169276; Accession No. gi167999540, Phypa ID 112415; Accession No. gi168049029, Phypa ID 194258; Accession No. gi168000434, Phypa ID 113212; Accession No. gi168038393, Phypa ID 190133; Accession No. gi168002106, Phypa ID 159190; Accession No. gi168015696, Phypa ID 122983; and Accession No. gi168052229, Phypa ID 27775.

Exemplary results are depicted in FIG. 3.

Example 5

Transgenic Moss Methods

This example describes methods for isolation of transgenic moss specific to the used vector. Necessary molecular characterization (locus genotyping and copy number evaluation) of such transgenic plants is not part of the present protocol, but follow standard techniques in common use in plant molecular biology field. Similarly, vector cloning (specific to each project) as well DNA amplification methods and restriction cut needed prior any moss specific procedure are described here. Maps and sequences of both vectors used in this particular project are available.

Transformation methods are consistent with Cove et al. (2008) The Moss *Physcomitrella patens*. A Novel Model System for Plant Development and Genomic Studies. IN: Emerging Model Organisms, a Laboratory Manual, Volume I. (Eds: D. A. Crotty and A. Gann). Chapter 3, pp. 69-104. Cold Spring Harbor Laboratory Press, New York. Desiccation assay methods are consistent with Werner et al 1991 Planta 186, 99-103; Charron and Quatrano 2009 Molecular Plant 2, 478-486; Khandelwal et al. 2010 Science 327, 546; and Yotsui et al. 2013 New Phytologist 199, 101-109.

Gene deletion methods are consistent with Cove et al. (2008) The Moss *Physcomitrella patens*, A Novel Model System for Plant Development and Genomic Studies, IN: Emerging Model Organisms, a Laboratory Manual, Vol I, Eds Crotty and Gann, Chapter 3, pp. 69-104, Cold Spring Harbor Laboratory Press, New York; Perroud and Quatrano 2008 The Plant Cell 20, 411-422; and Marella et al. 2006 The Plant Journal 46, 1032-1044. Desiccation assay methods are consistent with Werner et al 1991 Planta 186, 99-103; Charron and Quatrano 2009 Molecular Plant 2, 478-486; Khandelwal et al. 2010 Science 327, 546; and Yotsui et al. 2013 New Phytologist 199, 101-109.

Methods are described in three different protocols: protoplast production, protoplast transformation, and protoplast regeneration and plant selection. Such procedure was shown to work similarly with both strains used in the study Gg-1 (female) and R40 (male).

Protocols described hereafter are performed at room temperature (<22° C.) if not mentioned otherwise and in a sterile environment, e.g. vertical or horizontal laminar flow hood. Standard in vitro plant precautions concerning sterility (e.g. surface cleaning, reagent filtering and autoclaving) are required.

Protoplast Production.

Tissue from four Petri dishes of six-days old moss protonemata grown on BCDA medium in a Petri dish are harvested and transferred rapidly into 15 ml of 8.5% mannitol without letting the tissue dry. Five ml of driselase 2% (for a final driselase concentration of 0.5%) is added and incubated 45 minutes at room temperature with occasional gentle plate swirling. The suspension should be green after 45 minutes with a rapidly sedimenting colored component, protoplasts. The suspension is filtered through 100 μm sieve and let incubate at room temperature for 15 minutes. The suspension is filtered to 30-35 μm sieve and the flow-though containing isolated protoplasts are poured into a tube that can withstand low speed centrifugation (e.g. 50 ml conical "Falcon" tube). The tube is centrifuge for 5 minutes at 250 g to sediment the protoplast.

At this stage, a dark green pellet should be visible and the supernatant should be brownish (driselase color), not green. The supernatant is discarded and the pellet resuspended into 20 ml of mannitol 8.5% supplemented with 10 mM $CaCl_2$ (wash #1), then centrifuged 5 minutes at 250 g to sediment the protoplast. At this stage, a dark green pellet should be visible and the supernatant should be mostly clear. Resuspension of the pellet and centrifugation are repeated (wash #2).

The pellet is resuspended into 20 ml of mannitol 8.5% supplemented with 10 mM $CaCl_2$ and the protoplast number is evaluated in suspension using a hemacytometer (Fisher Scientific, USA, Cat. #0267110).

Thus is provided a suspension with a known number of protoplast that can be used for transformation (see below). Alternatively, protoplast can be plated on PRMB for a regeneration test. Typical protoplast yield is one million protoplasts per Petri dish plate.

Protoplast Transformation.

In a 15 ml sterile tube, 15 μg of vector DNA was resuspended in sterile TE with a maximum of 30 μl volume. This DNA can be produced by standard PCR amplification or plasmid prep amplification. With plasmid amplified DNA, however, the vector must be cut on each side of the transformation vector producing a linear, open-ended DNA fragment for transfection. This fragment type improves DNA integration and reduces the number of episomal transient transformants.

Added to the TE plus DNA is 300 μl of protoplast resuspended in MMM buffer. Protoplast concentration in the MMM buffer can be anywhere between $1.2 \times 10^6$ to $1.6 \times 10^6$ without affecting transformation efficiency, with the volume ratio for each component presented in this protocol. 300 μl of PEG transformation solution is added and mixed gently but thoroughly, producing visually uniform solution. The tube is incubated for 5 minutes in a 45° C. water bath then allowed to stand at room temperature for 10 minutes.

The PEG transformation solution is toxic to the protoplasts. Using a serial dilution approach (one dilution per minute), the transformation mix is added to successively five times 300 μl, then five times 1 ml of mannitol 8.5% supplemented with 10 mM $CaCl_2$. The tube is mixed gently by swirling after each dilution step. After dilution, the tube is allowed to stand at room temperature for 30 minutes. At this stage protoplasts have been transformed and are ready to be plated.

To concentrate, the protoplast suspension is centrifuged for 5 minutes at 250 g to sediment the protoplast. Supernatant is discarded and up to 2 ml of mannitol 8.5% supplemented with 10 mM $CaCl_2$ is added. Three ml of 45° C. PRMT (previously melted in the microwave and cooled down to 45° C. in a water bath) is added and mixed well by pipetting. 1.25 ml of the mix is quickly poured per PRMB plate overlaid with sterile cellophane (4 plates per transformation tube). Plates are allowed to stand for 30 minutes to one hour in a laminar flow hood (covered and sealed) before transferring the plate to the an incubator set at 25° C. and with a long light cycle (16 hours light/8 hours dark).

Plant Regeneration and Selection.

Week 1: Protoplast Regeneration.

Protoplasts are grown for 6 to 7 days on the plates poured for the transformation. Plates are observed for: 1) the number of dividing protoplasts, since this is the actually number that count to evaluate transformation efficiency (it should be as high as possible), and 2) bacterial or fungal contamination. After a week of growth, there should be between 2 to 15 cells per plant.

Week 2: First Selection.

Cellophane containing the regenerating protoplasts is transferred onto a BDCA plate supplemented with the appropriate antibiotic (for which resistance is present in the transformation vector) (e.g., Hygromicin B at 25 µg/L). Plates are incubated for a week in standard growth conditions. After this step, there should be left about 50 to 250 growing plants.

Week 3-4: Release from First Selection.

Cellophane containing living transformants and dead non-transformants are transferred onto a BDCA plate. Most of the growing moss plants are still transient transformants. The two weeks of selection release allows strong growth of the plants leading to dilution of the episomal element so such plant will end up to be antibiotic sensitive and die in the next selection step.

Week 5: Second Selection.

Cellophane is transferred onto BDCA plate supplemented with the appropriate antibiotic (for which resistance is present in the transformation vector) (e.g., Hygromicin B at 25 µg/l). This step will kill up to 90% of the remaining growing plants, leaving stable (or chromosome integrated) transformant.

Picking Transformants.

After 6-8 days of second selection, a stereoscope is used to pick any plant still growing and transfer such plant onto BCDA medium for tissue amplification. Filament (the most sensitive cell of a transient transformant) growing at the edge of plants are examined as an indicator of stably transformed plants.

Example 6

Overexpression of PHYPA ID 169276

The following example describes overexpression of Phypa ID 169276. Methods are consistent with Example 5 except as indicated otherwise.

A protein corresponding to Accession No. gi168047556, Phypa ID 169276, was over-expressed in Δabi3 and WT. Resulting over-expressing lines were subjected to a desiccation assay, in which tissues from 6-day-old over-expressing lines were treated with ABA (10 µM) for 24 hours, tissues were dried for 30 hours, rehydrated with sterile distilled water, and incubated for 1 week.

Figure 4:
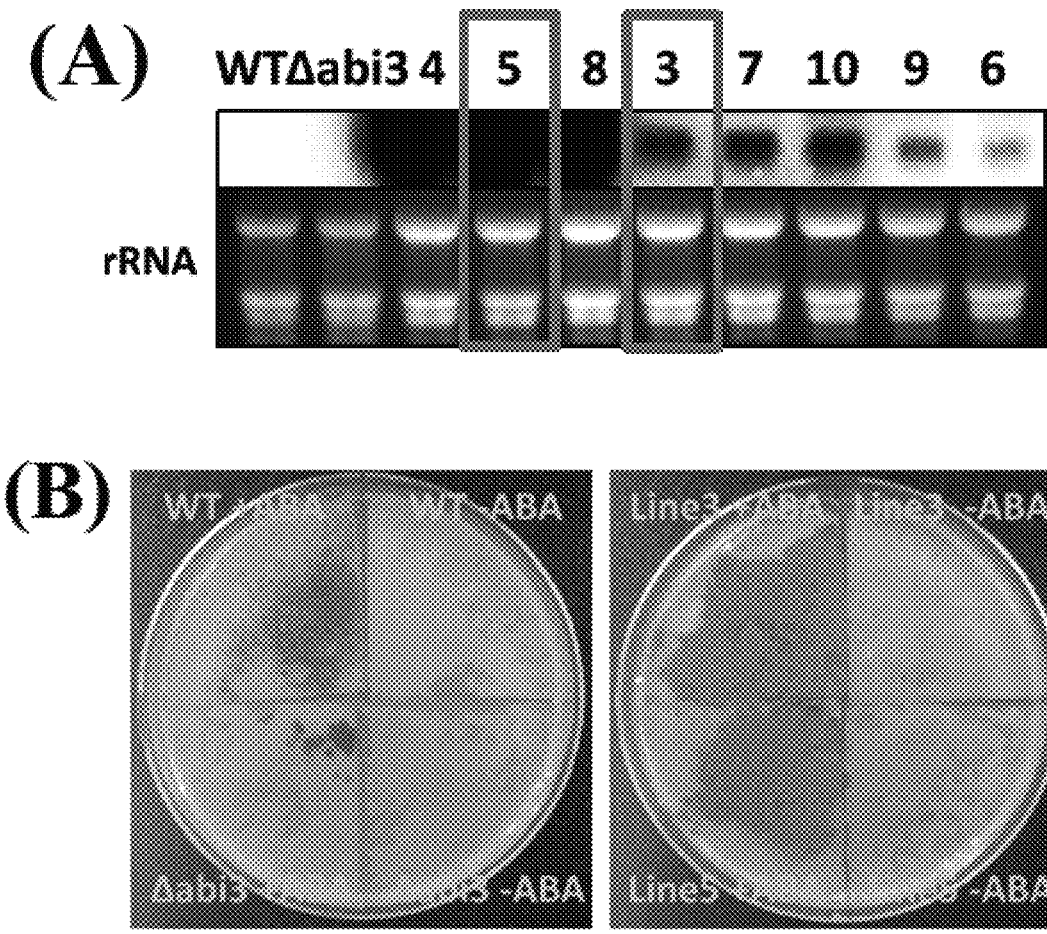
FIG. 4 is a series of images showing over-expression lines of Accession No. gi168047556, Phypa ID 169276, to A abi3 and resulting desiccation tolerance with ABA.

Results showed that over-expression lines of protein Phypa_169276 in provided desiccation tolerance when treated with ABA, similar to WT (see e.g., FIG. 4).

Figure 5:
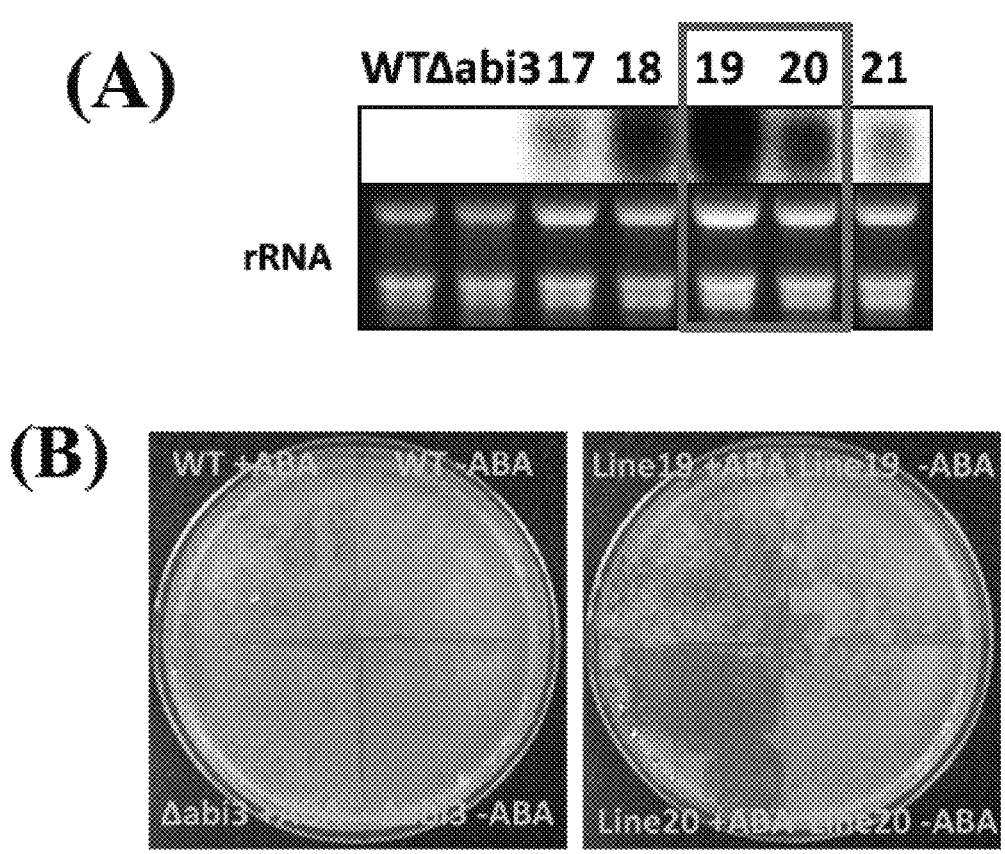
FIG. 5 is a series of images showing over-expression lines of Accession No. gi168047556, Phypa ID 169276, to WT and resulting stronger desiccation tolerance than WT with ABA.

Results also showed that over-expression lines of Phypa_169276 in WT acquired stronger desiccation tolerance with ABA than WT (see e.g., FIG. 5). These results support that Phypa_169276 plays a role in desiccation tolerance in *P. patens* vegetative tissue.

These results support that the gene regulatory pathway that requires both ABA and ABI3 control a relatively few proteins, and that these proteins can be used to increase desiccation tolerance, increase drought tolerance or increase water use efficiency in plant tissues.

Example 7

Knockout Studies

The following example describes knock out studies. Methods are consistent with Example 5 except as indicated otherwise.

Using targeted gene deletion techniques, deletion lines were developed for of the four genes shown to require both ABI3 and ABA as follows: Accession No. gi168047556, Phypa ID 169276 (SEQ ID NO: 1); Accession No. gi167999540, Phypa ID 112415 (SEQ ID NO: 2); Accession No. gi168000434, Phypa ID 113212 (SEQ ID NO: 5); and Accession No. gi168015696, Phypa ID 122983 (SEQ ID NO: 8).

Each knock-out line was subjected to a desiccation assay, in which tissues from 6-day-old knock-out lines were treated with ABA (10 µM) for 24 hours, tissues were dried for 30 hours, rehydrated with sterile distilled water, and incubated for 1 week.

Results showed that lines with Accession No. gi168047556, Phypa ID 169276 (SEQ ID NO: 1); Accession No. gi167999540, Phypa ID 112415 (SEQ ID NO: 2); or Accession No. gi168000434, Phypa ID 113212 (SEQ ID NO: 5) knocked out were approximately as tolerant to desiccation as controls.

But the line with Accession No. gi168015696, Phypa ID 122983 (SEQ ID NO: 8) knock out was clearly not as tolerant to desiccation as controls (or other knock outs) and exhibited reduced growth. Experiments with the SEQ ID NO: 8 knock out line were repeated with similar results.

Example 8

Multiple Knockout Studies

The following example describes prophetic multiple knock out studies. Methods are consistent with Example 5 except as indicated otherwise.

Using targeted gene deletion techniques, deletion lines are developed for combinations of the four genes shown to require both ABI3 and ABA as follows: Accession No. gi168047556, Phypa ID 169276 (SEQ ID NO: 1); Accession No. gi167999540, Phypa ID 112415 (SEQ ID NO: 2); Accession No. gi168000434, Phypa ID 113212 (SEQ ID NO: 5); and Accession No. gi168015696, Phypa ID 122983 (SEQ ID NO: 8).

Accession No. gi168015696, Phypa ID 122983 (SEQ ID NO: 8) knock out is tested in combination with each of the other three knock outs as well as in combinations of two of the three and all three. Exemplary knock out combinations are as follows:

SEQ ID NO: 8 and SEQ ID NO: 1
SEQ ID NO: 8 and SEQ ID NO: 2
SEQ ID NO: 8 and SEQ ID NO: 5
SEQ ID NO: 8, SEQ ID NO: 1, and SEQ ID NO: 2
SEQ ID NO: 8, SEQ ID NO: 1, and SEQ ID NO: 5
SEQ ID NO: 8, SEQ ID NO: 2, and SEQ ID NO: 5
SEQ ID NO: 8, SEQ ID NO: 1, SEQ ID NO: 2, and SEQ ID NO: 5

Results are expected to show that lines having multiple knockouts of the four genes show poorer performance in the desiccation assay or do not survive the desiccation assay, especially those knockouts of SEQ ID NO: 8 in combination with one or more gene knock outs.

SEQUENCE LISTING

SEQ ID NO: 1
Coding region of Phypa_169276
ATGGCAACAGTGAACGGTACATCAATAATGCAGACTACCAACTTAGCAATCACACCCGTGGCTGCAAGCCA
TTTGGGCTCGCGCACCGTCCAGCTCGGAGTCACACGCGTACTCTACAACGCCACCCTTACCACCAGGTCTG
CAAGGAGGCTCGTCGTGGTCGCCGCCGGAAACCCGGAACGAATTGACAACTTCGTCGACGGAGCCAGGAAA
GACGCCAGCCAAAACGCGAAGAACTTCGGCAACCAGGTGGCGGACGCCTTCGGCAACGCCCAGGAGACCGC
GAAGGACGTGGGTCGGGACATGGGCGCCAAGGCACAGGAAGCCGTCGACCAAGGCAGTAAGAAGGTCGACG
AGGCAGGAGACAAGGCCAGGGATGTAGCCAAGGAAGTGAGGGGCTCCACCGAGGATACCTTGAATGCTGCC
AAAGCAAACAACGGCCAATCTGTTGCGGACAAGGCGCAAAATGCTGCATCCAACGTGGGTGACAATTTGAA
GCAGAACTTCGATTACGGAACTGGGGCCGTGCAGAACGCCGCCGATGACGCGAGCAAAAACGTGAAAGACG
CCACTAACCGCAACCTCTAG SEQ ID NO: 2
Coding region of Phypa_112415
ATGTCGAGCCAGGAAGATCTTGACGCCAAGGCCGCCGCTGGAGAGACGGTGGTGCCCGGAGGCACTGGCGG
AAGGTCCTTTCAAGCTCAGAAGAACCTTGCAGAAGGCCGCAGCAAAGGAGGGCAAGCTCGTGCGGAGCAGC
TGGGTCATGAAGGATACGTAGAGATGGGCAAGAAGGGAGGCTCTGCTACAACTGACATGTCCAGTGGAGGC
GCTGCCGAGGCTGCCGGTCGCGGCATCGACGAGACCAAGTTCACCACCTAG SEQ ID NO: 3
Coding region of Phypa_27775
ATGAAGATGACGGTGGTTGCGGTGATGGCCGTGGTTCTGATCCTCGGTAGCGAGCTGCCTCGCTACTCGAG
CGCAGTTTCGAGCGAGGCTGAGGAGTTTGTGTCAGCGCACAACGCAGCGAGGGCTGATGTGGACGTAGGGC
CTTTGGTTTGGAGCCACAAGCTGGAGGATTACGCGCGCAAGTACGGGAGGAGCAGCGCGATCATCACAAT
TGCCGCCATGGTGCACTCGCGGGGTCCGTATGGGGAGAACCTTTTCTGGGGGCTACGGGAAGTCGTTTGCGCC
CGCGGATGCCGTGCGCTCGTGGGTGGATGAGAAACAGCACTACGACTACGACTCGAATTCCTGCGCGTCGG
GGAAGGTGTGCGGGCACTATACGCAGGTGGTGTGGGCGGACACAAAGGAGGTCGGGTGCGCTTCAATCACC
TGCCATGACAAGGCCACGTTCATCATCTGCAGCTATAATCCGCCTGGCAACTTCGTGGGCGAATGGCCATA
CAAGCGTGCCGGAACCAAGCATTCACATAGGCGATCTCATGAAAACGACGACTCTCGCACAAGCTCCCATA
AAACCACAGCCCAGACCACAGACGATGCCAACTCCGACCTCAAGCTCCGCTCAGTACATGAGTGTATGAGC
CAGTGTATGAATGATTGCTTCTCGATGTCTGGGTCCAGCCATCACCATCGCTCGAACTACTATCAGTAG SEQ ID NO: 4
Coding region of Phypa_194258
ATGGCTAATCGGTACTTCCCCAACACTATGCCAGATTATTCATTGAGTTTGGAAGGCTCAGAAGCGGATTA
TTCAGTGATGGATCCTGACACGCTGCTGGAGGTCGCCATGTCCATCAAAGATGAGGTGATACAAGCAACAT
GGATACGAAAAGGCCGAAGGGTTTCTGACCCCATTCTCTACACAGGGGTGTTGGGAACAGCTTTCTGTGC
TTTAAGGCATATCAAATTACAGGAAGCAAAGAGGATCTCACACTCTGCAGCGAGATCGTTGATAGTTGTAC
CGTTGCCGCTAAATCTTTGCACAAATACGTCACTTTTTTATGTGGGCAGCCAGGCATATATGCCTTAGGAG
CAGCAGCGGCAAAAAGCAGCGGGGATGAGCAAAGTCTTCATCCATATCTTCAGCTTTTCCATAAGGTTTCC
AAAAACCAAACTCTTGCTGTGGGAGCGGAAGAGGGTGGTATGGGAATGCCTTACGAACTTTTATATGGACG
TGCGGGGTTCTTATGGGCTGCTCTCTTTGTCAACAAGCATGTCGGCGAGGGGACCATTCCTTCGAGCACTA
CGGGTCCCATAGTTGATGCGATTTTAGCTGGCGGACGAGCTGGAGCTTCACAAACACAGTCTCCATTGATG
TATCAGTGGCACGGATCAAGATATTGGGGAGGAGCACATGGTCTGGCTGGTATCATGCACACTCTCATGCA
CTTTCCCTTGAACAAAAAGATGAAGAGGATGTCAAGGGAACACTACGATCATGATCGCGCGCCGCTTTC
CTAGTGGCAACTACCCATCCAGCGAGGGCAATGCAACAGACCGGTTGGTGCATTGGTGCCACGGAGCACCT
GGTATTGCCATGACTTTGTGCAAGGCGTCTAAGGTATTTCCTGATGAAATGGAGTTCCAACATGCAGCAGT
TGAAGCAGGAGATGTCGTATGGAGTCGAGGTCTACTTCGGAAGTTGGGCCTCTGTCATGGGATCAGTGGAA
ATACCTACGTCTTTCTGTCTTTGTACCAATCAACAGGAGGGAACACCACCTCTTCAGAGCTCAACAATTC
GCCACTTTCCTTCACAAAAACGCCAGAACGTTGATCGAGTCAGGAGAGATGCACGGCGGTGACCATCCCTA
CTCTCTGTTTGAAGGCTTGGCAGGAACTGCATGCCTCTTTTTTGACTTGACAAAACCAGAGATGGCAAGAT
TCCCTGCTTATGAGCTTTAG SEQ ID NO: 5
Coding region of Phypa_113212
ATGGCATCGTACAAGAGGACCTGTACAAGTGGCAACACGGCTTGCTGGGCACTGGACACATCAAATGGATT
GCATGACGCTCTCTGGGGCCTTGTCGTCATGCACCACCGCAATGCCATTACCCGAGTCTGGAAGCATCGC
TAGCATTTCGATCCTCTCCCTCGCCTTCAAAACCTCCGGGGAACACTCCAACCATCGCAGTCGTCATTCAA
GTGAATTCCATTCTCGTATTGCACCGAACAAGAACTTTTCTGTTGACCAGTGATCTTGAATCTTTCGTAAA
TTTTAGCTGTAGTCGGATTTACGTTTTCGCAATGGCGGAATTCCGACCCGCACAAGAGCAGTCGCAGCACC
CTGGAGAGGAGCATTTGATGGATCCTGTGCCTCGTCACCACGGAACCAACTACAAGGCTGCTGGCAAGTTG
AAGGGAAAGATAGCTCTAGTGACAGGCGGTGACTCCGGCATAGGTCGTGCCGTGGGCGTGCTCTTCACACG
AGAAGGTGCCACAGTGGCCTTCACATATGTGAAAGGAGCGGAAGAAAAGATGCGGTAGACACGATTAATT
TGCTGAAGCAGTACAAGGCAGAAGGTGGTGCGAAGGAGAACCTCTTGCAATTCCCTGCGATCTAGGATTC
GACGAGCAGTGCAAGAAGGTTGTAGACAAAGTCGTTGAGAAGTATGGCCGAATCGACATCCTGGTCAACAA
TGCGGCAGAGCAGCACGTCGTGGAGAACATTGAGGATCTCCAGCCTGAGCAGCTGGAGCGGACGTTCCGCA
CCAACATCTTCTCCCAGTTTTACCTCGTAAGACATGCCTTGAAGCATATGAAAGAGGGTAGCTGTATTATT
AATACGACTTCCGTTAATGCATTCAAGGGCAACACCACACTTCTAGACTACACTTCCACAAAGGGCGCCAT
TCTTGCCTTCACTCGGGGACTGGCTCTTCAGCTTGTCAAGCGCGGAATTCGAGTAAATGCGGTAGCGCCAG
GCCCAATTTGGACGCCGCTCATTCCAGCATCAATGGGTCAAGATCGCCTGAGAAGATGAAATCCTTCGGT
TCGCAATGCCCAATGGGCCGTGCTGGTGAGCCAGAGGAAATCGCAACGGCGTATGTTTTCCTTGCTTCAGA
GGATTCCTCTTACTTCACTGGCCAAACCCTGCACCCGAACGGTGGAATAGTTGTGAACGCATAA SEQ ID NO: 6
Coding region of Phypa_190133
ATGGTGAATCAAGCATTGGAGGCTATGCCGAAGCTTAAGTTGAACACTGGCACATGTATTTCCGCCGTTGG
GCTAGGAACCTGGCAGGCGGATCCAGGCTTGGTTAAACAAGCTGTCAAGGAAGCTGTAAAAGTTGGGTACC
GCCACATCGACTGCGCCAAGGCTTACAAAAACGAGGACGAGGTGGGAGAAGCTTTGCAGGAGCTTTTCAAG
GAAGGCGTTGTTAAGCGTGAAGACTTGTGGATCACGTCGAAACTTTGGTGCACTGACCACAACCCTGCGGA

SEQUENCE LISTING

```
TGTGGAGCCGGCATTGGACGGGTCGATTGAGCGTTTGCAATGTGGCTACCTTGATCTGTACCTGATGCATT
GGCCGGTCGCCTTGAAGAAGGATGCTCAAGGCACAGGTCCAGATGACTTTGCTCCTCTCAATGTCGCGGCG
ACATGGGCAGCTATGGAAAAGTGCTACGAGAAGGGGAAAGCGAAGGCTATCGGAATCAGTAACTTCTCTGT
AGAGAAAACGAAGGACTTGTTGTCTAAATGCAAAGTACGACCTGCTGTGAACCAGGTGGAATGCCACCCTC
TTTGGCAGCAGAAGAAGTTGTGGCCATACTTAAAGTCCGAGGGCATTCACTTGACAGCTTACTCTCCAATC
GGATCCTCAAACAGTCCCTTCGCAACAATTAACGTCTTAGAGCTTCCCACAGTCACGAAATTGGCTGAGAA
ATACAAAAGGTCTCCATCACAGATAGTTCTCCGATGGAACATCCAACAAGGTCATAGCGTGCTGCCAAAGA
GCACTCACGCTGATCGGCTTGCGTCCAACATTGAGATCTTCGACTTCGAACTCAATGAAGAAGATCTCAAG
GAATTCGACAAAATTGAGCAGCACCGCCTTCTCCTTGGAGACGACATGTGGATAAATGACAAAACCAGTCC
ATACAAGACGGTGGAGGAGCTCTGGGACGGAGACATCTAA

SEQ ID NO: 7
Coding region of Phypa_159190
ATGGCGAAGTCCGCCGCCGCCGTGGTGATATGTGTGCTTTTCTTGGGGGTGTTCATGGGGACTCCTGCTGT
GGCGAGCAGGAAGATGTGCAAAGGAGCGGTTTCCCTCGCCATTGTGCGCTTTGCATTCCTACCACAGAGT
CGTTGTTCATGAAGCACGATGGGAAGCACTCGTGCGCGTATAATTTGACTAACGGTGACAGAGCTGTTGGT
GTGGCGTATAACTTGGATGATGACGTAGAGTCTCGCCGGTCTGAGCTTACTGCTGTTTTTGCTGACTACGA
CAAGGTTTACGAAGGGAAAGACTGCCTGAACACAATCCAGATTAGTGCCCTGCTCACTTTAGATGCTAAAC
GTGCCCTTGATAGAGCTGCCAAAAGCGTTAAGTCCTTAGACGACCAGTGCTGCGACGTCATGGCCGTTTTT
GGCGACATCCAACACTCTGGAGGCAAGGACGTGTACCAGGAAAATGCGTTTGATGACTTCATTGAAGCTGT
GAGTGCCAAGAAATGGGAGAAGGGAGTCGAGTTGCTGGATAGAACCAGGTGGTGCAATGACAACAAAGATA
GATGTGATGACGATAAAAAGATCATCTCTGAAGGTTGCAAGGGTACATTCGCCACTGGAGTCATTGCTCAG
GTCACCGACGCTCTGAAAGCTTAG SEQ ID NO: 8
Coding region of Phypa_122983
ATGATGGGTACTCGGAACGTGTTGGTTTTTGCTGTTGGGTTGTTTCTTGTGCTGAGCTTTGCTGCAGCTAG
CGGCAGTAAACATGACGACAACCATGAGCTGATGATCGGGGGGCTGGACATGACTACAAGTGCCGGCCCG
GGAACTATACCACCACCAAGGACAAGGAGCTCACGCAGGTTGCTCTGAACTTGGAGTATTTCGAAGCGGAG
TATTTCTTGTGGGGAGCTTACGGCTATGGTTTGGACAAGATTGCTCCCTACTTGGTCGATGGCGGTCCCCC
CCCCATTGGTGCTCAGAAGGCCAATTTGGACGCTTACTATACCGATATCTACATTCAGATGGGGCTTCAGG
AAGTTGGACATCTCAGGGCGATCAAGAGAGCTTTGGGTGATCCTCCCAGGTGTGCATTCCCTCGCACTCAG
CTGGACATTAGCAAAAAGACCTGGGCCGATACGATGGACAAGGCGTTCCTGCAGACTTTCGGCGAGAAGCT
GAACCCTCCCTATGATCCTTATGAAGACAGCTTGAAGTACCTCATCTCCACGTACACCATTCCCTACGTTG
GGTTGACGGGATACGTCGGCGCTAACCCCGAGTTGAAGGGATACAATGCCAAGAAGCTTGTGGCTGGTTTG
CTGGGTGTGGAGTCGGGTCAAGACGCTATCATTCGCACCGAAATGTACCGCCAGAAGAACAAGAAGGTCAG
CCCGTACAAGTACACCGTGGCGGATTTCAGCAACGCCATTTCCAACTTGAGGAACAACTTGTCCCACGCTT
TCGTTGACGAAGGATTGGTGGTGCCAAATGAGCTGGGTGCTGAAATGATGGTGACTGGTAACATATTGTCT
GCTGACAACGACTCTCTCTCCTACCCTCGTACTGCCGAGCAGGTGTTCGAAACTGTTTACGGGACCGGAGA
TGCTTCCAAGCCCGGAGGCTTCTATCCCAAGGGCTGTCAGGGTGTCATCGCCGCGAGTTACCTTGATTAG
```

What is claimed is:

1. A transgenic plant engineered to have increased desiccation tolerance, increased drought tolerance or increased water use efficiency, the plant transformed with an artificial DNA construct comprising, as operably associated components in the 5' to 3' direction of transcription:
   a promoter that functions in a plant;
   a polynucleotide consisting of SEQ ID NO: 8; and
   a transcriptional termination sequence;
   wherein the transgenic plant has an increased desiccation tolerance, increased drought tolerance or increased water use efficiency compared to a plant without the DNA construct.

2. The transgenic plant of claim 1, wherein
   (a) the DNA construct further comprises at least one polynucleotide selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7; or
   (b) the plant comprises a second DNA construct comprising a polynucleotide selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

3. The transgenic plant of claim 2, wherein the plant comprises SEQ ID NO: 8 and one or more of SEQ ID NO: 1, SEQ ID NO: 2, SEQ ID NO: 3, SEQ ID NO: 4, SEQ ID NO: 5, SEQ ID NO: 6, or SEQ ID NO: 7.

4. The transgenic plant of claim 2, wherein the plant comprises SEQ ID NO: 8 and one or more of SEQ ID NO: 1, SEQ ID NO: 2, or SEQ ID NO: 5.

5. The transgenic plant of claim 4, wherein the plant comprises:
   SEQ ID NO: 8 and SEQ ID NO: 1;
   SEQ ID NO: 8 and SEQ ID NO: 2;
   SEQ ID NO: 8 and SEQ ID NO: 5;
   SEQ ID NO: 8, SEQ ID NO: 1, and SEQ ID NO: 2;
   SEQ ID NO: 8, SEQ ID NO: 1, and SEQ ID NO: 5;
   SEQ ID NO: 8, SEQ ID NO: 2, and SEQ ID NO: 5; or
   SEQ ID NO: 8, SEQ ID NO: 1, SEQ ID NO: 2, and SEQ ID NO: 5.

6. The transgenic plant of claim 1, wherein the promoter is an inducible promoter.

7. The transgenic plant of claim 1, wherein the promoter is a tissue-specific promoter.

8. The transgenic plant of claim 7, wherein the promoter is a seed-specific promoter.

9. The transgenic plant of claim 1, wherein the drought tolerance is increased by at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, or at least about 1000%, as compared to a plant not comprising the DNA construct.

10. The transgenic plant of claim 1, wherein the water use efficiency is increased by at least about 10%, at least about 20%, at least about 30%, at least about 40%, at least about 50%, at least about 60%, at least about 70%, at least about 80%, at least about 90%, at least about 100%, at least about 250%, at least about 500%, at least about 750%, or at least about 1000%, as compared to a plant not comprising the DNA construct.

11. The transgenic plant of claim 1, wherein the plant is selected from the group consisting of maize, bean, soybean, wheat, barley, hay, rice, peanut, cotton, tomato, cucurbit, okra, eggplant, pepper, sugar beet, sugarcane, cassava, potatoes, palm, rapeseed, sunflower, coconut, olive, flax, safflower, sesame, apple, pear, grape, strawberry, blackcurrant, redcurrant, gooseberry, guava, lucuma, chili pepper, pomegranate, kiwifruit, cranberry, blueberry, blackberry, raspberry, boysenberry, banana, plum, cherry, peach, apricot, mango, orange, lime, lemon, grapefruit, pineapple, fig, mulberry, hedge apple, osage-orange, and breadfruit.

12. A plant part of the transgenic plant of claim 1.

13. An artificial DNA construct comprising, as operably associated components in the 5' to 3' direction of transcription:
   a promoter that functions in a plant;
   a polynucleotide consisting of SEQ ID NO: 8; and
   a transcriptional termination sequence;
   wherein the promoter is heterologous to SEQ ID NO: 8.

14. A method of increasing desiccation tolerance, drought tolerance, or water use efficiency of a plant comprising:

transforming a plant with an artificial DNA construct comprising, as operably associated components in the 5' to 3' direction of transcription:
a promoter that functions in a plant;
a polynucleotide consisting of SEQ ID NO: 8; and
a transcriptional termination sequence;
wherein the transgenic plant has an increased desiccation tolerance, increased drought tolerance, or increased water use efficiency compared to a plant without the DNA construct.

* * * * *